(12) United States Patent
Kohno et al.

(10) Patent No.: US 8,273,748 B2
(45) Date of Patent: Sep. 25, 2012

(54) AMINO ALCOHOL DERIVATIVE AND IMMUNOSUPPRESIVE AGENT HAVING SAME AS AN ACTIVE INGREDIENT

(75) Inventors: Yasushi Kohno, Tochigi (JP); Kiyoshi Fujii, Tochigi (JP); Tatsuhiro Saito, Tochigi (JP); Kazuhiko Kuriyama, Tochigi (JP); Tokutarou Yasue, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 187 days.

(21) Appl. No.: 12/310,018

(22) PCT Filed: Aug. 7, 2007

(86) PCT No.: PCT/JP2007/065426
§ 371 (c)(1),
(2), (4) Date: Feb. 6, 2009

(87) PCT Pub. No.: WO2008/018447
PCT Pub. Date: Feb. 14, 2008

(65) Prior Publication Data
US 2010/0010000 A1    Jan. 14, 2010

(30) Foreign Application Priority Data
Aug. 8, 2006 (JP) ................ 2006-215281

(51) Int. Cl.
*A61K 31/50* (2006.01)
*A61K 31/235* (2006.01)
(52) U.S. Cl. ............................ 514/252.1; 514/533
(58) Field of Classification Search .............. None
See application file for complete search history.

(56) References Cited

U.S. PATENT DOCUMENTS

| | | | |
|---|---|---|---|
| 5,447,922 A | 9/1995 | Lawrence et al. | |
| 5,604,229 A | 2/1997 | Fujita et al. | |
| 5,948,820 A | 9/1999 | Fujita et al. | |
| 6,004,565 A | 12/1999 | Chiba et al. | |
| 6,214,873 B1 | 4/2001 | Adachi et al. | |
| 6,489,331 B1 | 12/2002 | Shimada et al. | |
| 6,960,692 B2 | 11/2005 | Kohno et al. | |
| 6,963,012 B2 | 11/2005 | Kohno et al. | |
| 7,456,157 B2 | 11/2008 | Kohno et al. | |
| 7,482,491 B2 * | 1/2009 | Kohno et al. | 564/355 |
| 2002/0040050 A1 | 4/2002 | Xu et al. | |
| 2002/0091105 A1 | 7/2002 | Mandala et al. | |
| 2002/0143034 A1 | 10/2002 | Taniguchi et al. | |
| 2003/0236297 A1 | 12/2003 | Nishi et al. | |
| 2004/0058894 A1 | 3/2004 | Doherty et al. | |
| 2004/0067908 A1 | 4/2004 | Nakade et al. | |
| 2004/0087662 A1 | 5/2004 | Bigaud et al. | |
| 2004/0110728 A1 | 6/2004 | Macdonald et al. | |
| 2004/0138462 A1 | 7/2004 | Sakurai et al. | |
| 2004/0147490 A1 | 7/2004 | Albert et al. | |
| 2004/0224941 A1 | 11/2004 | Seko et al. | |
| 2004/0235794 A1 | 11/2004 | Nakade et al. | |
| 2004/0242654 A1 | 12/2004 | Kohno et al. | |
| 2004/0248952 A1 | 12/2004 | Pan et al. | |
| 2004/0254222 A1 | 12/2004 | Kohno et al. | |
| 2005/0009786 A1 | 1/2005 | Pan et al. | |
| 2005/0020837 A1 | 1/2005 | Doherty et al. | |
| 2005/0033055 A1 | 2/2005 | Bugianesi et al. | |
| 2005/0043386 A1 | 2/2005 | Nishi et al. | |
| 2005/0107345 A1 | 5/2005 | Doherty et al. | |
| 2005/0222422 A1 | 10/2005 | Lynch et al. | |
| 2005/0245575 A1 | 11/2005 | Chen et al. | |
| 2006/0046979 A1 | 3/2006 | Foster et al. | |
| 2006/0089334 A1 | 4/2006 | Budhu et al. | |
| 2006/0135622 A1 | 6/2006 | Kohno et al. | |
| 2006/0135786 A1 | 6/2006 | Saha et al. | |
| 2006/0148830 A1 | 7/2006 | Terakado et al. | |
| 2006/0148844 A1 | 7/2006 | Nakade et al. | |
| 2006/0160771 A1 | 7/2006 | Kohno et al. | |
| 2006/0161005 A1 | 7/2006 | Doherty et al. | |
| 2006/0166940 A1 | 7/2006 | Buehlmayer et al. | |
| 2006/0211656 A1 | 9/2006 | Albert et al. | |
| 2006/0211658 A1 | 9/2006 | Hinterding et al. | |
| 2006/0252741 A1 | 11/2006 | Colandrea et al. | |
| 2006/0264403 A1 | 11/2006 | Albert | |
| 2007/0010494 A1 | 1/2007 | Ehrhardt et al. | |

(Continued)

FOREIGN PATENT DOCUMENTS

JP    2002-53575    2/2002

(Continued)

OTHER PUBLICATIONS

STN Search Report (Accession No. 2003:282516).*
Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
International Search Report dated Oct. 2, 2007 in the International (PCT) Application PCT/JP2007/065426 of which the present application is the U.S. National Stage.
Blam et al., Integrating Anti-Tumor Necrosis Factor Therapy in Inflammatory Bowel Disease: Current and Future Perspectives, Am. J. Gastroenterology, 2001, vol. 96, No. 7, pp. 1977-1997.

(Continued)

*Primary Examiner* — Craig Ricci
(74) *Attorney, Agent, or Firm* — Wenderoth, Lind & Ponack, L.L.P.

(57) ABSTRACT

An amino alcohol derivative useful as an excellent immunosuppressive agent is provided.
As a result of intensive research to create a highly safe compound which has an excellent immunosuppressive activity, it was discovered that an amino alcohol derivative represented by the general formula (1),

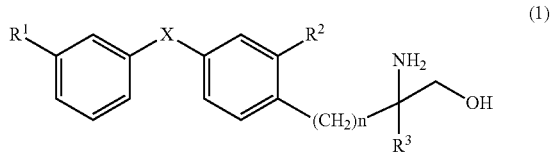

has excellent immunosuppressive activity.

16 Claims, No Drawings

U.S. PATENT DOCUMENTS

| | | | |
|---|---|---|---|
| 2007/0043014 | A1 | 2/2007 | Doherty et al. |
| 2007/0088002 | A1 | 4/2007 | Lynch et al. |
| 2007/0135501 | A1 | 6/2007 | Hinterding et al. |
| 2007/0149597 | A1 | 6/2007 | Nishi et al. |
| 2007/0167410 | A1 | 7/2007 | Pan et al. |
| 2007/0167425 | A1 | 7/2007 | Nakade et al. |
| 2007/0191468 | A1 | 8/2007 | Nishi et al. |
| 2007/0203100 | A1 | 8/2007 | Pan et al. |
| 2007/0225260 | A1 | 9/2007 | Hinterding et al. |
| 2008/0025973 | A1 | 1/2008 | Fleenor et al. |
| 2008/0027508 | A1 | 1/2008 | Chu |
| 2008/0032923 | A1 | 2/2008 | Kudou et al. |
| 2008/0153882 | A1 | 6/2008 | Nishi et al. |
| 2008/0161410 | A1 | 7/2008 | Kusters et al. |
| 2008/0200438 | A1 | 8/2008 | Albert et al. |
| 2008/0207584 | A1 | 8/2008 | Habashita et al. |
| 2008/0207941 | A1 | 8/2008 | Tsubuki et al. |
| 2008/0249093 | A1 | 10/2008 | Colandrea et al. |
| 2009/0023797 | A1 | 1/2009 | Azzaoui et al. |

FOREIGN PATENT DOCUMENTS

| | | | |
|---|---|---|---|
| JP | 2002-316985 | | 10/2002 |
| JP | 2003-137894 | | 5/2003 |
| JP | 2003-267936 | | 9/2003 |
| JP | 2004-137208 | | 5/2004 |
| JP | 2004-307439 | | 11/2004 |
| JP | 2004-307440 | | 11/2004 |
| JP | 2004-307441 | | 11/2004 |
| JP | 2004-307442 | | 11/2004 |
| JP | 2005-47899 | | 2/2005 |
| JP | 2005-247691 | | 9/2005 |
| WO | 01/98301 | | 12/2001 |
| WO | WO 03/029184 | * | 4/2003 |
| WO | 03/040097 | | 5/2003 |
| WO | 03/051876 | | 6/2003 |
| WO | 2004/026817 | | 4/2004 |
| WO | WO 2004/026817 | * | 4/2004 |
| WO | 2005/014525 | | 2/2005 |
| WO | 2005/014603 | | 2/2005 |
| WO | 2005/063671 | | 7/2005 |
| WO | 2006/041015 | | 4/2006 |
| WO | 2006/063033 | | 6/2006 |
| WO | 2006/129688 | | 12/2006 |
| WO | 2007/043433 | | 4/2007 |
| WO | 2007/043568 | | 4/2007 |
| WO | 2007/091501 | | 8/2007 |
| WO | 2007/126042 | | 11/2007 |

OTHER PUBLICATIONS

Keller et al., Immunomodulator FTY720 Induces Myofibroblast Differentiation via the Lysophospholipid Receptor S1P3 and Smad3 Signaling, Am. J. Pathology, Jan. 2007, vol. 170, No. 1, pp. 281-292.
Yasuyuki Igarashi, Sphingosine-1-Phosphate as an Intercellular Signaling Molecule, Ann. NY Acad. Sci., 1998, vol. 845, pp. 19-31.
Jacobs et al., Intramuscular Interferon Beta-1a for Disease Progression in Relapsing Multiple Sclerosis, Ann. Neurol., 1996, vol. 39, No. 3, pp. 285-294.
Weinshenker et al., A Randomized Trial of Plasma Exchange in Acute Central Nervous System Inflammatory Demyelinating Disease, Ann. Neurol., 1999, vol. 46, No. 6, pp. 878-886.
Ganem et al., The Molecular Biology of the Hepatitis B Virus, Annu. Rev. Biochem., 1987, vol. 56 pp. 651-693.
Kaneko et al., Sphingosine-1-phosphate receptor agonists suppress concanavalin A-induced hepatic injury in mice, Biochem. and Biophys. Res. Commun., 2006, vol. 345, pp. 85-92.
Okazaki et al., Molecular Cloning of a Novel Putative G Protein-Coupled Receptor Expressed in the Cardiovascular System, Biochem. and Biophys. Res. Commun., 1993, vol. 190, No. 3, pp. 1104-1106.
Klein et al., Total Synthesis and Antifungal Evaluation of Cyclic Aminohexapeptides, Bioorg. Med. Chem., 2000, vol. 8, pp. 167-1696.
Hashimoto et al., 13-Phenylselenoalanine as a dehydroalanine precursor-efficient synthesis of alternariolide (AM-toxin I), Chem. Commun., 1996, pp. 1139-1140.
Levkau et al., High-Density Lipoprotein Stimulates Myocardial Perfusion in Vivo, Circulation, 2004, vol. 110, pp. 3355-3359.
Salomone et al., $S1P_3$ receptors mediate the potent constriction of cerebral arteries by sphingosine-1-phosphate, Eur. J. Pharmacol., 2003, vol. 469, pp. 125-134.
Heneghan et al., Current and Novel Immunosuppressive Therapy for Autoimmune Hepatitis, Hepatology, 2002, vol. 35, No. 1, pp. 7-13.
Francis V. Chisari, Cytotoxic T Cells and Viral Hepatitis, J. Clin. Invest., Apr. 1997, vol. 99, No. 7, pp. 1472-1477.
Kiuchi et al., Synthesis and Immunosuppressive Activity of 2-Substituted 2-Aminopropane-1,3-diols and 2-Aminoethanols, J. Med. Chem., 2000, vol. 43, pp. 2946-2961.
Brinkmann et al., The Immune Modulator FTY720 Targets Sphingosine 1-Phosphate Receptors, J. Biol. Chem., 2002, vol. 277, No. 24, pp. 21453-21457.
Sanna et al., Sphingosine 1-Phosphate (S1P) Receptor Subtypes $S1P_1$ and $S1P_3$, Respectively, Regulate Lymphocyte Recirculation and Heart Rate, J. Biol. Chem., Apr. 2, 2004, vol. 279, No. 14, pp. 13839-13848.
Forrest et al., Immune Cell Regulation and Cardiovascular Effects of Sphingosine 1-Phosphate Receptor Agonists in Rodents are Mediated via Distinct Receptor Subtypes, J. Pharm. Exp. Ther., 2004, vol. 309, No. 2, pp. 758-768.
George C. Ebers, Randomised double-blind placebo-controlled study of interferon β-1a in relapsing/remitting multiple sclerosis, Lancet, Nov. 7, 1998, vol. 352, pp. 1498-1501.
Takuwa et al., Subtype-specific, differential activities of the EDG family receptors for sphingosine-1-phosphate, a novel lysophospholipid mediator, Mol. Cell. Endocrinol., 2001, vol. 177, pp. 3-11.
Fried et al., Peginterferon Alfa-2a Plus Ribavirin for Chronic Hepatitis C Virus Infection, N. Engl. J. Med., Sep. 26, 2002, vol. 347, No. 13, pp. 975-982.
Mailliard et al., Suppressing Hepatitis B without Resistance—So Far, So Good, N. Engl. J. Med., Feb. 27, 2003, vol. 348, No. 9, pp. 848-850.
Niessen et al., Dentritic cell PAR1-S1P3 signalling couples coagulation and inflammation, Nature, Apr. 3, 2008, vol. 452, No. 3, pp. 654-658.
INFB Multiple Sclerosis Study Group, Interferon beta-1b is effective in relapsing-remitting multiple sclerosis. I. Clinical results of a multicenter, randomized, double-blind, placebo-controlled trial, Neurology, Apr. 1993, vol. 43, pp. 655-661.
Paty et al., Interferon beta-1b is effective in relapsing-remitting multiple sclerosis. II. MRI analysis results of a multicenter, randomized, double-blind, placebo-controlled trial, Neurology, Apr. 1993, vol. 43, pp. 662-667.
Johnson et al., Copolymer 1 reduces relapse rate and improves disability in relapsing-remitting multiple sclerosis: Results of a phase III multicenter, double-blind, placebo-controlled trial, Neurology, Jul. 1995, vol. 45, pp. 1268-1276.
Zivadinov et al., Effects of IV methylprednisolone on brain atrophy in relapsing-remitting MS, Neurology, 2001, vol. 57, pp. 1239-1247.
Goodin et al., Disease modifying therapies in multiple sclerosis; Report of the Therapeutics and Technology Assessment Subcommittee of the American Academy of Neurology and the MS Council for Clinical Practice Guidelines, Neurology, 2002, vol. 58, pp. 169-178.
Rudick et al., Management of Multiple Cclerosis, N. Engl. J. Med., Nov. 27, 1997, vol. 337, No. 22, pp. 1604-1611.
Daniel K. Podolsky, Inflammatory Bowel Disease, N. Engl. J. Med., Aug. 8, 2002, vol. 347, No. 6, pp. 417-429.
Kappos et al., Oral Fingolimod (FTY720) for Relapsing Multiple Sclerosis, N. Engl. J. Med., Sep. 14, 2006, vol. 355, No. 11, pp. 1124-1140.
Viscido et al., Inflammatory bowel diseases: clinical update of practical guidelines, Nucl. Med. Commun., 2005, vol. 26, No. 7, pp. 649-655.
Gon et al., $S1P_3$ receptor-induced reorganization of epithelial tight junctions comprises lung barrier integrity and is potentiated by TNF, PNAS, Jun. 28, 2005, vol. 102, No. 26, pp. 9270-9275.
Saito et al., Hepatitis C virus infection is associated with the development of hepatocellular carcinoma, Proc. Natl. Acad. Sci. USA, Sep. 1990, vol. 87, pp. 6547-6549.

Mandala et al., Alteration of Lymphocyte Trafficking by Sphingosine-1-Phosphate Receptor Agonists, Science, Apr. 2, 2002, vol. 296, pp. 346-349.

Hinterding et al., Synthesis of Chiral Analogues of FTY720 and its Phosphate, Synthesis, 2003, No. 11, pp. 1667-1670.

Campbell et al., The Synthesis of Novel Amino Acids via Hydroboration-Suzuki Cross Coupling, Tetrohedron Letters, 1999, vol. 40, pp. 5263-5266.

Collier et al., The direct synthesis of novel enantiomerically pure α-amino acids in protected form via suzuki cross-coupling, Tetrahedron Letters, 2000, vol. 41, pp. 7115-7119.

Long et al., Enantioselective syntheses of homophenylalanine derivatives via nitron 1,3-dipolar cycloaddition reactions with styrenes, Tetrahedron Letters, 2001, vol. 42, pp. 5343-5345.

Shimizu et al., KRP-203, a Novel Synthetic Immunosuppressant, Prolongs Graft Survival and Attenuates Chronic Rejection in Rat Skin and Heart Allografts, Circulation, 2005, vol. 111, pp. 222-229.

Takahashi et al., a Novel Immunomodulator KRP-203 Combined with Cyclosporine Prolonged Graft Survival and Abrogated Transplant Vasculopathy in Rat Heart Allografts, Transplant. Proc., 2005, vol. 37, pp. 143-145.

Kohno, Yasushi et al., "Discovery of KRP-203, a potent and orally active new type of immunosuppressant, sphingosine-1-phosphate receptor agonist", From Abstracts of Papers, $229^{th}$ ACS National Meeting, San Diego, CA, U.S., Mar. 13-17, 2005.

English translation of Office Action issued Oct. 21, 2010 in Russian Application corresponding to U.S. Appl. No. 12/083,224.

Julien Davaille et al., "Sphingosine 1-Phosphate Triggers Both Apoptotic and Survival Signals for Human Hepatic Myofibroblasts", J. Biol. Chem., vol. 277, No. 40, pp. 37323-37330 (2002).

* cited by examiner

AMINO ALCOHOL DERIVATIVE AND IMMUNOSUPPRESIVE AGENT HAVING SAME AS AN ACTIVE INGREDIENT

TECHNICAL FIELD

The present invention relates to an amino alcohol derivative useful as an immuno suppressive agent, and a salt and a hydrate thereof.

BACKGROUND ART

Immunosuppressive agents are widely utilized as a treatment agent for autoimmune diseases such as rheumatoid arthritis, nephritis, degenerative knee arthritis, and systemic lupus erythematosus, chronic inflammatory diseases such as inflammatory bowel disease, and allergic diseases such as asthma and dermatitis. In particular, with the progress in medical technology, in recent years large numbers of transplant operations of tissues, organs and the like are being performed. In such medical practice, whether the post-transplant rejection reaction can be well controlled determines whether the transplant is successful or not. Immunosuppressive agents are playing an important role in this area as well.

In organ transplants, antimetabolites represented by azathioprine and mycophenolate mofetil, calcineurin inhibitors represented by cyclosporine A and tacrolimus, and adrenocortical hormones represented by prednisolone are used. However, in some cases the effectiveness of these pharmaceuticals has been insufficient, or blood concentration monitoring has been essential in order to avoid serious side effects such as kidney damage. Therefore, in terms of their effectiveness and side effects, these pharmaceuticals have not always been satisfactory.

Furthermore, to alleviate the side effects of the immunosuppressive agent and to obtain a sufficient immunosuppressive activity, multiple drug therapy using a plurality of pharmaceuticals having different action mechanisms is typical. Thus, there is also a need for development of a new type of pharmaceutical which has an action mechanism different from that of the above-described immunosuppressive agents.

Recently, reports of various amino alcohol derivatives, such as 2-amino-1,3-propanediol derivatives and 2-aminoethanol derivatives, as novel immunosuppressive agents have been drawing attention. However, these amino alcohol derivatives themselves do not have an immunosuppressive activity. These drugs are metabolized after being administered into the body to produce a phosphate, and it is this phosphate which is the true physiologically active substance. The produced phosphate exhibits agonistic activity and antagonist activity against various sphingosine 1-phosphate (S1P) receptors. Among them, in 2002 it was reported for the first time that the agonistic activity against $S1P_1$ receptors expresses an immunosuppressive activity by regulating white blood cell migration (Non-patent Documents 1 and 2). It has also been disclosed that, in addition to being effective for various organ transplants and GVHD, the series of derivatives introduced in these Non-patent documents are effective for rheumatoid arthritis, lupus nephritis, systemic lupus erythematosus, chronic thyroiditis, multiple sclerosis, myasthenia gravis, type I and II diabetes mellitus, autoimmune diseases such as Crohn's disease, allergic diseases such as atopic dermatitis, allergic rhinitis, allergic conjunctivitis, and allergic contact dermatitis, and inflammatory diseases such as inflammatory bowel disease or ulcerative colitis (Patent Documents 1 and 2). Since these reports, not only amino alcohol derivatives, but various compounds, such as amino phosphate derivatives and amino carboxylic acid derivatives, have been disclosed as immunosuppressive agents or $S1P_1$ to $S1P_5$ receptor regulators focused on $S1P_1$ receptors (Patent Documents 3 to 66).

Furthermore, since $S1P_4$ receptors are largely concentrated in immunocompetent cells, such as leukocytes, and in organs which greatly contribute to the immune system, it is suggested that $S1P_4$ receptors have a strong contribution to the immune system. In fact, compounds having an $S1P_4$ agonistic activity have been disclosed for autoimmune diseases such as SLE and rheumatism, asthma, allergic diseases such as atopic dermatitis, and inflammatory disease remedies (Patent Documents 34, 39, and 50).

Thus, while a great deal of attention is being paid to S1P receptor agonist drugs which may have hidden potential in a wide variety of medical applications, not all S1P receptor agonist drugs provide a desirable action on the body.

For example, an S1P receptor agonist drug which has exhibited effectiveness in clinical trials in suppressing organ transplant rejection was found to produce bradycardia as a side effect after administration. This effect was reported to probably be caused by agonistic activity against the $S1P_3$ receptor (Non-patent Documents 3 and 4). Furthermore, agonistic activity against the $S1P_3$ receptor has also been reported to cause in experimental animal models effects such as obstruction of myocardial blood flow (Non-patent Document 5), cerebral arterial spasms (Non-patent Document 6), and pulmonary edema (Non-patent Document 7).

[Patent Document 1] WO 0218395 pamphlet
[Patent Document 2] WO 02076995 pamphlet
[Patent Document 3] WO 9408943 pamphlet
[Patent Document 4] Japanese Patent Application Laid-Open No. Hei 9-2579602
[Patent Document 5] WO 0206268 pamphlet
[Patent Document 6] Japanese Patent Application Laid-Open No. 2002-53572
[Patent Document 7] Japanese Patent Application Laid-Open No. 2002-167382
[Patent Document 9] WO 02076995 pamphlet
[Patent Document 10] Japanese Patent Application Laid-Open No. 2003-137894
[Patent Document 11] WO 03040097 pamphlet
[Patent Document 12] WO 02064616 pamphlet
[Patent Document 13] WO 02062389 pamphlet
[Patent Document 14] Japanese Patent Application Laid-Open No. 2002-316985
[Patent Document 15] Japanese Patent Application Laid-Open No. 2003-267936
[Patent Document 16] WO 03051876 pamphlet
[Patent Document 17] WO 03061567 pamphlet
[Patent Document 18] WO 03062248 pamphlet
[Patent Document 19] WO 03062252 pamphlet
[Patent Document 20] WO 03073986 pamphlet
[Patent Document 21] WO 03074008 pamphlet
[Patent Document 22] WO 03105771 pamphlet
[Patent Document 23] WO 04010949 pamphlet
[Patent Document 24] WO 04024673 pamphlet
[Patent Document 25] WO 04058149 pamphlet
[Patent Document 26] WO 04071442 pamphlet
[Patent Document 27] WO 04096752 pamphlet
[Patent Document 28] WO 04096757 pamphlet
[Patent Document 29] WO 04103279 pamphlet
[Patent Document 30] WO 04103306 pamphlet
[Patent Document 31] WO 04103309 pamphlet
[Patent Document 32] WO 04110979 pamphlet
[Patent Document 33] WO 04113330 pamphlet
[Patent Document 34] WO 04074297 pamphlet

[Patent Document 35] WO 05014603 pamphlet
[Patent Document 36] WO 05020882 pamphlet
[Patent Document 37] WO 04002531 pamphlet
[Patent Document 38] WO 05032465 pamphlet
[Patent Document 39] WO 05041899 pamphlet
[Patent Document 40] WO 05058848 pamphlet
[Patent Document 41] WO 05070886 pamphlet
[Patent Document 42] WO 05082089 pamphlet
[Patent Document 43] WO 05082841 pamphlet
[Patent Document 44] WO 05021503 pamphlet
[Patent Document 45] WO 05040091 pamphlet
[Patent Document 46] WO 05085179 pamphlet
[Patent Document 47] WO 05118523 pamphlet
[Patent Document 48] WO 05014525 pamphlet
[Patent Document 49] WO 06020951 pamphlet
[Patent Document 50] WO 06001463 pamphlet
[Patent Document 51] WO 03029184 pamphlet
[Patent Document 52] WO 03029205 pamphlet
[Patent Document 53] WO 04026817 pamphlet
[Patent Document 54] WO 04074297 pamphlet
[Patent Document 55] WO 05021503 pamphlet
[Patent Document 56] Japanese Patent Application Laid-Open No. 2004-307439
[Patent Document 57] Japanese Patent Application Laid-Open No. 2004-307440
[Patent Document 58] Japanese Patent Application Laid-Open No. 2004-307441
[Patent Document 59] Japanese Patent Application Laid-Open No. 2004-307442
[Patent Document 60] WO 06041015 pamphlet
[Patent Document 61] Japanese Patent Application Laid-Open No. 2004-137208
[Patent Document 62] Japanese Patent Application Laid-Open No. 2005-41867
[Patent Document 63] Japanese Patent Application Laid-Open No. 2005-47899
[Patent Document 64] WO 05040091 pamphlet
[Patent Document 65] WO 05063671 pamphlet
[Patent Document 66] WO 05079788 pamphlet
[Non-patent Document 1] S. Mandalaetal., Science, 296, 346 (2002).
[Non-patent Document 2] V. Brinkmann et al., J. Biol. Chem., 277, 21453 (2002).
[Non-patent Document 3] M. G. Sanna et al., J. Biol. Chem., 279, 13839 (2004).
[Non-patent Document 4] M. Forrestetal., J. Pharmacol. Exp. Ther., 309, 758 (2004).
[Non-patent Document 5] B. Levkau et al., Circulation, 110, 3358 (2004).
[Non-patent Document 6] S. Salomoneet al., Eur. J. Pharmacol. 469, 125 (2003).
[Non-patent Document 7] Y. Gon et al., PNAS 102, 9270 (2005).

DISCLOSURE OF THE INVENTION

Problems to be Solved by the Invention

It is an object of the present invention to provide an amino alcohol derivative having excellent immunosuppressive activity and few side effects.
Means for Solving the Problems
As a result of intensive research concerning immunosuppressive agents which have a different action mechanism to that of antimetabolites and calcineurin inhibitors, the present inventors discovered that a novel amino alcohol derivative has high safety and excellent immunosuppressive activity, thereby completing the present invention.

Specifically, the present invention relates to:

1) An amino alcohol derivative, represented by the general formula (1),

[Chemical formula 1]

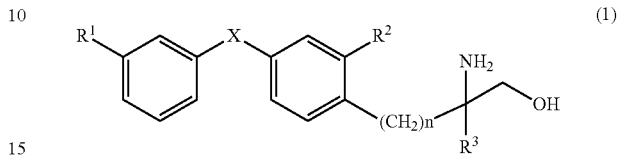

[wherein $R^1$ represents a chlorine atom or a straight-chain alkyl group having 1 to 3 carbon atoms or trifluoromethyl group, $R^2$ represents a fluorine atom or a chlorine atom, $R^3$ represents a straight-chain alkyl group having 1 to 3 carbon atoms, X represents an oxygen atom or a sulfur atom, and n denotes 2 or 3], or a pharmaceutically acceptable salt or hydrate thereof.

2) The amino alcohol derivative according to 1), wherein the compound represented by the general formula (1) is a compound represented by the general formula (1a),

[Chemical formula 2]

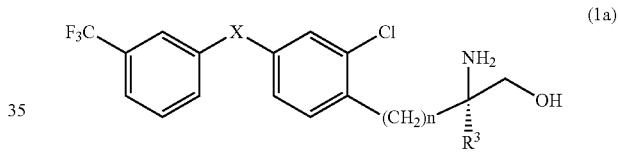

[wherein $R^3$, X, and n are as described above], or a pharmaceutically acceptable salt or hydrate thereof.

3) The amino alcohol derivative according to 1) or 2), wherein in the general formulae (1) or (1a), $R^3$ is a methyl group, or a pharmaceutically acceptable salt or hydrate thereof.

4) The amino alcohol derivative according to 1), wherein the compound represented by the general formula (1) is, (R)-2-amino-5-[2-chloro-4-(3-trifluoromethylphenoxy)phenyl]-2-methylpentan-1-ol, (R)-2-amino-5-[2-chloro-4-(3-trifluoromethylphenylthio)phenyl]-2-methylpentan-1-ol, (R)-2-amino-4-[2-chloro-4-(3-trifluoromethylphenoxy)phenyl]-2-methylbutan-1-ol, (R)-2-amino-4-[2-chloro-4-(3-trifluoromethylphenylthio)phenyl]-2-methylbutan-1-ol, (R)-2-amino-5-[2-chloro-4-(3-ethylphenylthio)phenyl]-2-methylpentan-1-ol, (R)-2-amino-5-[2-fluoro-4-(3-trifluoromethylphenylthio)phenyl]-2-methylpentan-1-ol, or (R)-2-amino-5-[2-chloro-4-(3-trifluoromethylphenylthio)phenyl]-2-propylpentan-1-ol, or a pharmaceutically acceptable salt or hydrate thereof.

5) The amino alcohol derivative according to 1), or a pharmaceutically acceptable salt or hydrate thereof, which is obtainable by a step of allowing a compound represented by the general formula (2),

[Chemical formula 3]

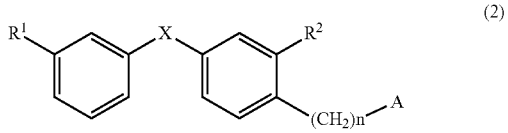

[wherein $R^1$ represents a chlorine atom or a straight-chain alkyl group having 1 to 3 carbon atoms or trifluoromethyl group, $R^2$ represents a fluorine atom or a chlorine atom, A represents a halogen atom, X represents an oxygen atom or a sulfur atom, and n denotes 2 or 3] and a compound represented by the general formula (10),

[Chemical formula 4]

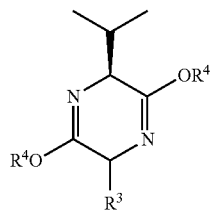

[wherein $R^3$ represents a straight-chain alkyl group having 1 to 3 carbon atoms and $R^4$ represents an alkyl group having 1 to 6 carbon atoms] to act in the presence of a base, and a step of subjecting the resultant product to acidolysis, then further protecting a nitrogen atom with a t-butoxycarbonyl group, reducing, and deprotecting the nitrogen atom, or a pharmaceutically acceptable salt or hydrate thereof.

6) A pharmaceutical comprising the amino alcohol derivative, or a pharmaceutically acceptable salt or hydrate thereof, according to any of 1) to 5) as an active ingredient.
7) The pharmaceutical according to 6), which is an immunosuppressive agent.
8) The pharmaceutical according to 6), which is a rejection reaction preventive or treatment agent in organ transplants or bone marrow transplants.
9) A pharmaceutical comprising the amino alcohol derivative, or a pharmaceutically acceptable salt or hydrate thereof, according to any of 1) to 5) and a calcineurin inhibitor in combination.

Effect of the Invention

According to the present invention, an amino alcohol derivative having excellent immunosuppressive activity and safety can be provided. The compound of the present invention is useful as a preventive or treatment agent for rejection in organ transplants or bone marrow transplants, a preventive or treatment agent for autoimmune diseases such as inflammatory bowel disease, systemic lupus erythematosus, Crohn's disease, nephrotic syndrome, glomerular sclerosis, glomerular nephritis, multiple sclerosis, and myasthenia gravis, a preventive or treatment agent for rheumatoid arthritis, a preventive or treatment agent for psoriasis, allergic contact dermatitis, and atopic dermatitis, a preventive or treatment agent for hepatitis, hepatic steatosis, toxic liver injury, liver cirrhosis or diabetes mellitus-derived liver disease, a preventive or treatment agent for allergic rhinitis, allergic conjunctivitis and the like, and a preventive or treatment agent for pulmonary fibrosis, idiopathic interstitial pneumonia, and bronchial asthma.

BEST MODE FOR CARRYING OUT THE INVENTION

In the present invention, the straight-chain alkyl group having 1 to 3 carbon atoms of $R^1$ and $R^3$ is a methyl group, an ethyl group, or an n-propyl group.

From the perspective of obtaining high safety, $R^1$ is preferably an ethyl group, a propyl group, or a trifluoromethyl group, and more preferably is a trifluoromethyl group. Furthermore, $R^3$ is preferably a methyl group, and n is preferably 3.

Furthermore, from the perspective of obtaining high immunosuppressive activity, X is preferably a sulfur atom, and the configuration of $R^3$ is preferably a configuration produced as the principal product via the below-described synthesis route B (using the compound (10)).

In the present invention, examples of pharmaceutically acceptable salts include acid addition salts such as hydrochloride salts, hydrobromic acid salts, acetic acid salts, trifluoroacetic acid salts, methanesulfonic acid salts, citric acid salts, or tartaric acid salts.

The compound according to the present invention represented by the general formula (1) can be produced, for example, via the synthesis route A shown below.

<Synthesis Route A>

[Chemical formula 5]

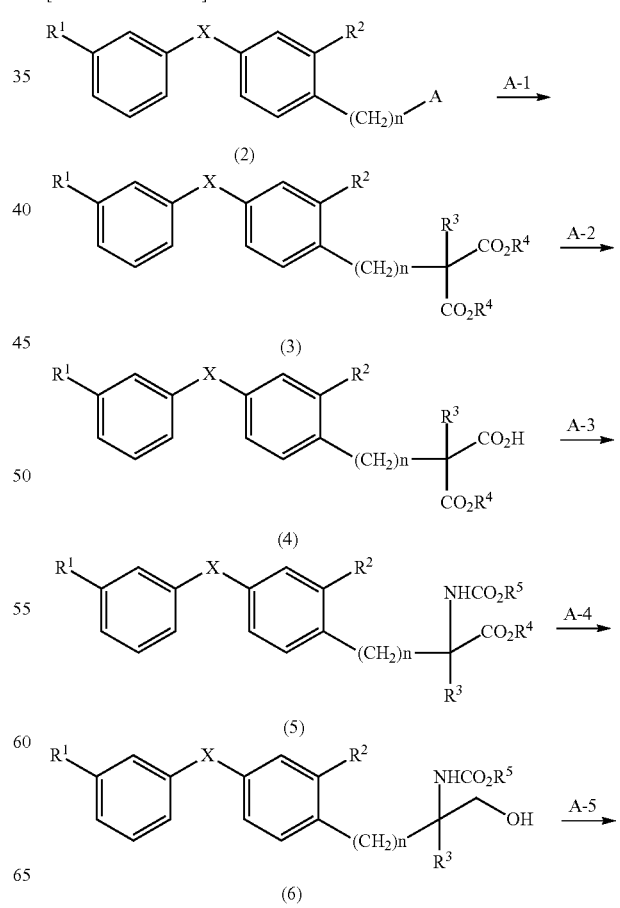

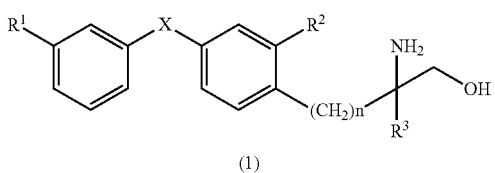

(1)

In the synthesis route A, the compound represented by the general formula (3),

[Chemical formula 6]

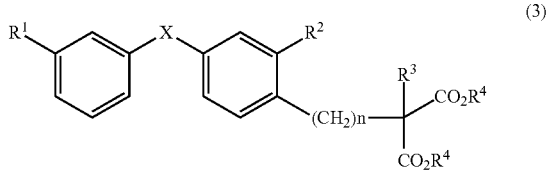

(3)

[wherein $R^1$, $R^2$, $R^3$, $R^4$, X, and n are as described above], can be produced by allowing a compound represented by the general formula (2),

[Chemical formula 7]

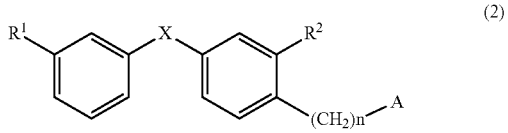

(2)

[wherein $R^1$, $R^2$, A, X, and n are as described above], and a compound represented by the general formula (7),

[Chemical formula 8]

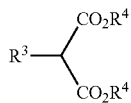

(7)

[wherein $R^3$ and $R^4$ are as described above] to act in the presence of a base (step A-1).

The reaction can be carried out using methanol, ethanol, 1,4-dioxane, dimethylsulfoxide (DMSO), N,N-dimethylformamide (DMF), tetrahydrofuran (THF) and the like as a reaction solvent, in the presence of an inorganic base such as sodium hydride, potassium hydride, sodium methoxide, sodium ethoxide, sodium t-butoxide, potassium methoxide, potassium ethoxide, potassium t-butoxide, and potassium carbonate, at 0° C. to reflux temperature as the reaction temperature, and preferably at 80° C. to 100° C.

In the synthesis route A, the compound represented by the general formula (4),

[Chemical formula 9]

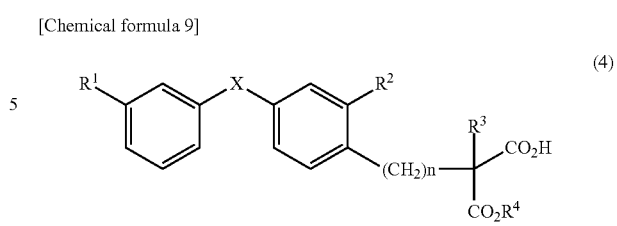

(4)

[wherein $R^1$, $R^2$, $R^3$, $R^4$, X, and n are as described above], can be produced by hydrolyzing the compound represented by the general formula (3) (step A-2).

The reaction can be carried out in the presence of a base such as aqueous sodium hydroxide, aqueous potassium hydroxide, and aqueous lithium hydroxide, using methanol, ethanol, 1,4-dioxane, DMF, DMSO, THF and the like as a reaction solvent, at a reaction temperature of 0° C. to reflux temperature. Preferably, the reaction is carried out using potassium hydroxide as the base, in an ethanol solvent, by reacting at 50° C.

Although the compound according to the present invention is preferably a specific optically-active substance, when the optical resolution is carried out is not especially limited. At this stage, optical resolution may be carried out by HPLC using a chiral column, whereby the desired compound having a chiral center can be obtained.

In the synthesis route A, the compound represented by the general formula (5),

[Chemical formula 10]

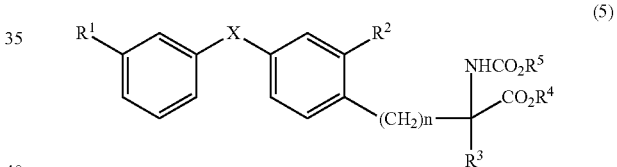

(5)

[wherein $R^5$ represents an alkyl group having 1 to 6 carbon atoms, and $R^1$, $R^2$, $R^3$, $R^4$, X, and n are as described above], can be produced by subjecting the compound represented by the general formula (4) to Curtius rearrangement (step A-3).

In the reaction, typical methods for converting a carboxyl group into a carbamate may be employed. For example, a method which combines, for example, chloroethyl carbonate and $NaN_3$, or oxalyl chloride and $NaN_3$, or a method which uses only diphenylphosphoryl azide (DPPA) may be utilized. The reaction is preferably carried out by, after heating diphenylphosphoryl azide to reflux in the presence of an organic base, such as triethylamine, in benzene or toluene solvent, charging the resultant product with an alcohol represented by the general formula (8), $R^5OH$ (8)

[herein $R^5$ is as described above], and continuing to heat the resultant solution under stirring, or, after removing the solvent used in the above reaction, such as benzene or toluene, by evaporation, by heating to reflux using the alcohol represented by the general formula (8) as a reaction solvent.

At this stage, optical resolution may be carried out by HPLC using a chiral column, whereby the desired compound having a chiral center can be obtained.

In the synthesis route A, the compound represented by the general formula (6),

[Chemical formula 11]

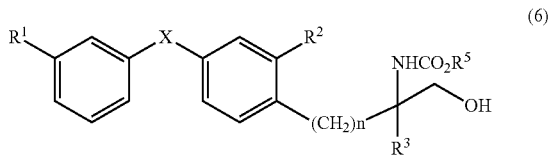

(6)

[wherein $R^1$, $R^2$, $R^3$, $R^5$, X, and n are as described above], can be produced by reducing the compound represented by the general formula (5) (step A-4).

The reaction can be carried out using borane, an alkyl borane derivative like 9-borabicyclo[3.3.1]nonane (9-BBN), or a metal hydride complex compound, such as diisobutylaluminum hydride ($(iBu)_2AlH$), sodium borohydride ($NaBH_4$), lithium borohydride ($LiBH_4$), and lithium aluminum hydride ($LiAlH_4$), preferably $LiBH_4$, using THF, 1,4-dioxane, ethanol, or methanol as a reaction solvent, at a temperature of 0° C. to reflux temperature, and preferably at room temperature.

Furthermore, at this stage also, optical resolution may be carried out by HPLC using a chiral column, whereby the desired compound having a chiral center can be obtained.

In the synthesis route A, the compound represented by the general formula (1) can be produced by subjecting the compound represented by the general formula (6) to acidolysis or hydrolysis (step A-5).

The reaction can be carried out at room temperature to reflux temperatures in an inorganic acid or organic acid, such as hydrochloric acid, hydrobromic acid, methanesulfonic acid, acetic acid, and trifluoroacetic acid, or at room temperature to reflux temperature by adding an organic solvent such as methanol, ethanol, THF, and 1,4-dioxane to an inorganic acid or organic acid, such as hydrochloric acid, hydrobromic acid, methanesulfonic acid, acetic acid, and trifluoroacetic acid. The reaction may also be carried out in the presence of a base such as aqueous sodium hydroxide, aqueous potassium hydroxide, and aqueous lithium hydroxide, using methanol, ethanol, THF, 1,4-dioxane, DMSO, and DMF as a reaction solvent, at a temperature of 0° C. to reflux temperature, and preferably 80 to 100° C.

In the synthesis route A, among the compounds represented by the general formula (5), compounds in which $R^5$ represents a t-butyl group, specifically, a compound represented by the general formula (5a),

[Chemical formula 12]

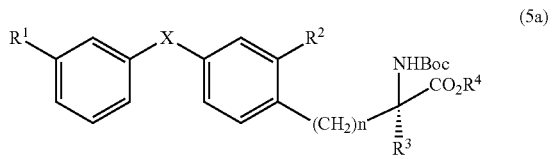

(5a)

[wherein Boc represents a t-butoxycarbonyl group, and $R^1$, $R^2$, $R^3$, $R^4$, X, and n are as described above], and among the compounds represented by the general formula (6) in the synthesis route A, compounds in which $R^5$ represents a t-butyl group, specifically, a compound represented by the general formula (6a),

[Chemical formula 13]

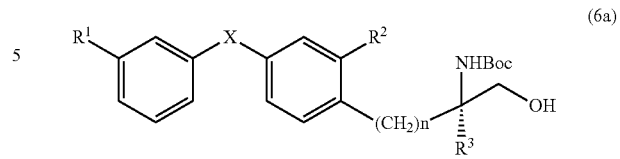

(6a)

[wherein $R^1$, $R^2$, $R^3$, X, Boc, and n are as described above], can be produced by the synthesis route B.

<Synthesis Route B>

[Chemical formula 14]

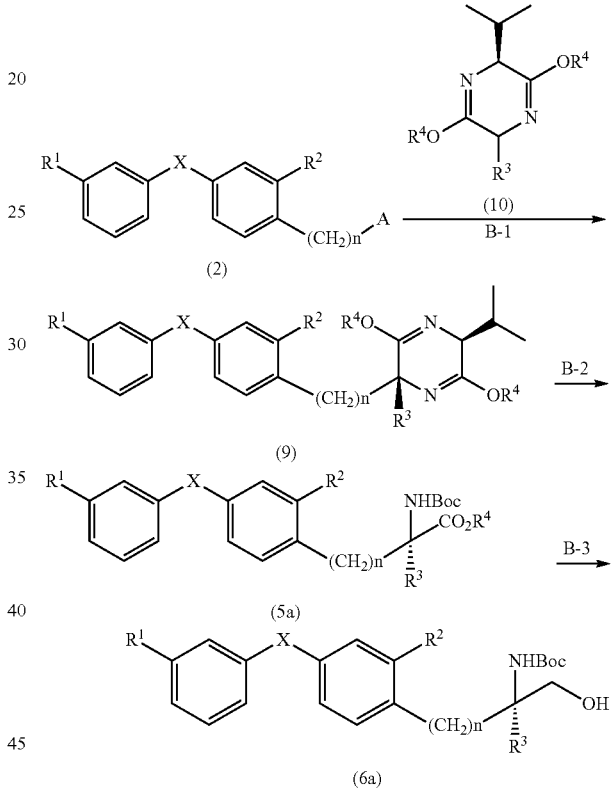

In the synthesis route B, the compound represented by the general formula (9),

[Chemical formula 15]

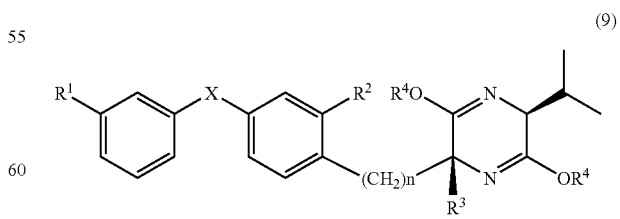

(9)

[wherein $R^1$, $R^2$, $R^3$, $R^4$, X, and n are as described above], can be produced by allowing a compound represented by the general formula (2) and a compound represented by the general formula (10),

[Chemical formula 16]

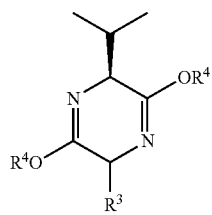

(10)

[wherein $R^3$ and $R^4$ are as described above] to act in the presence of a base (step B-1).

The reaction can be carried out using a reaction solvent such as 1,4-dioxane, THF, and ether, using a base such as n-butyllithium and lithium diisopropyl amide, preferably n-butyllithium, and treating a compound represented by the general formula (10) at −78° C., then allowing a compound represented by general formula (2) to act at −78° C., and reacting while gradually increasing the temperature to room temperature.

In the synthesis route B, the compound represented by the general formula (5a) can be produced by subjecting a compound represented by the general formula (9) to acidolysis, and then protecting the nitrogen atom with a t-butoxycarbonyl group (Boc group) (step B-2).

In the reaction, an amino ester can be obtained using methanol, ethanol, THF, 1,4-dioxane, or ethyl acetate in which hydrochloric acid is dissolved, and preferably 1,4-dioxane containing hydrochloric acid, by reacting at reflux temperature, then neutralizing with a base. Furthermore, it is preferred to allowing it to act with $Boc_2O$ at 0° C. to room temperature using ethyl acetate, THF, DMF, 1,4-dioxane, methylene chloride, chloroform, methanol, ethanol, acetonitrile or the like as a solvent.

In the synthesis route B, the compound represented by the general formula (6a) can be produced by reducing a compound represented by the general formula (5a) (step B-3).

The reaction can be carried out using borane, an alkyl borane derivative like 9-BBN, or a metal hydride complex compound, such as $(iBu)_2AlH$, $NaBH_4$, $LiBH_4$, and $LiAlH_4$, preferably $LiBH_4$, using THF, 1,4-dioxane, ethanol, or methanol as a reaction solvent, at a temperature of 0° C. to reflux temperature, and preferably at room temperature.

It is noted that concerning the synthesis method of the compound represented by the general formula (2), the compound may be produced by the methods described in the respective pamphlets of WO 03029184, WO 03029205, WO 04026817, WO 04074297, and WO 050444780.

The compound of the present invention is metabolized in the body to produce a phosphate (phosphoric acid ester). As a result, the compound of the present invention is useful as an excellent preventive or treatment agent for rejection in organ transplants or bone marrow transplants, a preventive or treatment agent for autoimmune diseases such as inflammatory bowel disease, systemic lupus erythematosus, Crohn's disease, nephrotic syndrome, glomerular sclerosis, glomerular nephritis, multiple sclerosis, and myasthenia gravis, a preventive or treatment agent for rheumatoid arthritis, a preventive or treatment agent for psoriasis, allergic contact dermatitis, and atopic dermatitis, a preventive or treatment agent for hepatitis, hepatic steatosis, toxic liver injury, liver cirrhosis or diabetes mellitus-derived liver disease, a preventive or treatment agent for allergic rhinitis, allergic conjunctivitis and the like, and a preventive or treatment agent for pulmonary fibrosis, idiopathic interstitial pneumonia, and bronchial asthma.

In the case of using as above, the required dose of course depends on the administration method, the specific condition to be treated, and the desired effects. However, generally, a daily dose of about 0.03 to 2.5 mg per kg of body weight is preferred. For mammals such as humans, the recommended daily dose is in the range of about 0.5 mg to about 100 mg. Preferably, administration is carried out in divided doses of four times or less per day, or in retard form. A suitable unit dose form for oral administration includes about 1 to 50 mg of active ingredient.

The compound of the present invention may be administered by an arbitrary conventional route, especially enterally, for example orally, for example in the form of a tablet or a capsule, or parenterally, for example in the form of an injectable solution or a suspension, locally, for example in the form of a lotion, a gel, an ointment, or a cream, or nasally or in the form of a suppository. A pharmaceutical composition containing the compound of the present invention in free form or a pharmaceutically acceptable salt thereof together with at least one kind of pharmaceutically acceptable carrier or diluent may be produced by a conventional method of mixing with the pharmaceutically acceptable carrier or diluent. Furthermore, the compound of the present invention is also useful when used together with an immunosuppressive agent and/or a pharmaceutical which has an anti-inflammatory activity having a different mechanism. Examples of pharmaceuticals which can be used together include immunosuppressive agents used in the treatment and prevention of acute or chronic rejection of allogeneic transplants and heterologous transplantats, inflammatory diseases, and autoimmune diseases, immunosuppressive agents having an immunomodulatory activity and/or anti-inflammatory agents having an anti-inflammatory or malignant cell growth inhibition activity. Specific examples include the calcineurin inhibitors cyclosporin A and FK506, the mTor inhibitors rapamycin, 40-O-(2-hydroxymethyl)-rapamycin, CCI779, and ABT578, the ascomycins ABT281 and ASM981 which have an immunosuppressive activity, mycophenolic acid, mycophenolate mofetil, azathioprine, mizoribine, cyclophosphamide and the like. Further examples include the antifolate methotrexate, adrenal cortical steroids which exhibit broad anti-inflammatory activity, auranofin, actarit, mesalazine, or sulfasalazine etc. which have an immunomodulatory activity, infliximab which is an anti-TNFα antibody, MRA which is an anti-IL-6 receptor antibody, Natarizumab which is an anti-integrin antibody and the like.

EXAMPLES

Next, the present invention will be described with the following specific examples. However, the present invention is not limited by these examples.

Furthermore, as the intermediates and the like represented by the general formula (2), the compounds in the pamphlets of WO 03029184, WO 03029205, WO 04026817, WO 04074297, and WO 050444780 may be utilized. Furthermore, (5S)-3,6-diethoxy-5-isopropyl-2-methyl-2,5-dihydropyrazine, (5S)-3,6-dimethoxy-5-isopropyl-2-methyl-2,5-dihydropyrazine, and (5S)-2-allyl-3,6-diethoxy-5-isopropyl-2, 5-dihydropyrazine may be synthesized according to Ulrich Shollkopf et. al, Synthesis 969 (1981) and Chunrong Ma et. al., J. Org. Chem., 66, 4525 (2001). Intermediates and the like which were newly synthesized based on the experiment procedures described in these reference documents will now be described as the following reference examples.

Reference Example 1

2-Fluoro-4-(3-trifluoromethylphenylthio)benzaldehyde

[Chemical formula 17]

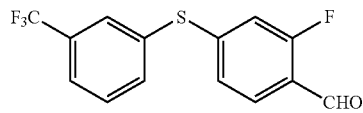

Under an argon atmosphere, ethyldiisopropylamine (7.0 mL), tris(dibenzylideneacetone)dipalladium(0) chloroform adduct (518 mg), xantphos (578 mg), and 3-trifluoromethylthiophenol (3.56 g) were added at room temperature into a solution of 4-bromo-2-fluorobenzaldehyde (4.06 g) in 1,4-dioxane (42 mL), and the resultant solution was heated to reflux for 5 hours. To the reaction solution added water, extracted with ethyl acetate, washed with water and saturated brine in that order, and then dried over anhydrous sodium sulfate. The solvent was evaporated, and the resultant residue was purified by silica gel column chromatography (hexane:ethyl acetate 30:1) to obtain the target product (4.08 g) as a colorless oil.
$^1$H-NMR (CDCl$_3$, 400 MHz): δ 6.86 (1H, dd, J=10, 1.8 Hz), 7.02 (1H, dd, J=7.9, 1.8 Hz), 7.58 (1H, t, J=7.9 Hz), 7.68-7.73 (2H, m), 7.76 (1H, t, J=7.9 Hz), 7.80 (1H, s), 10.26 (1H, s)
EIMS (+): 300 [M]$^+$.

Reference Example 2

2-Chloro-4-(3-chlorophenylthio)benzaldehyde

[Chemical formula 18]

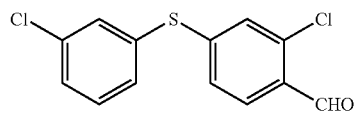

3-Chlorobenzenethiol and 2-chloro-4-fluorobenzaldehyde were reacted according to the same experiment procedures as in Reference Example 1 of the pamphlet of WO 03029205 to obtain the target product as a colorless oil.
$^1$H-NMR (CDCl$_3$, 400 MHz): δ 7.11 (1H, dd, J=9.2, 1.8 Hz), 7.17 (1H, d, J=1.8 Hz), 7.36-7.44 (3H, m), 7.52 (1H, t, J=1.8 Hz), 7.80 (1H, d, J=7.9 Hz), 10.37 (1H, s)
EIMS (+): 282 [M]$^+$.

Reference Example 3

2-Chloro-4-(3-methylphenoxy)benzaldehyde

[Chemical formula 19]

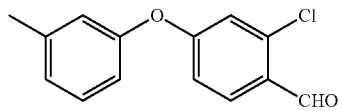

m-Cresol and 2-chloro-4-fluorobenzaldehyde were reacted according to the same experiment procedures as in Reference Example 1 of the pamphlet of WO 03029184 to obtain the target product as a colorless powder.
$^1$H-NMR (CDCl$_3$, 400 MHz): δ 2.38 (3H, s), 6.87-6.96 (4H, m), 7.07 (1H, d, J=7.3 Hz), 7.31 (1H, t, J=7.6 Hz), 7.90 (1H, d, J=8.60 Hz), 10.36 (1H, s)
EIMS (+): 246 [M]$^+$.

Reference Example 4

2-Chloro-4-(3-ethylphenylthio)benzaldehyde

[Chemical formula 20]

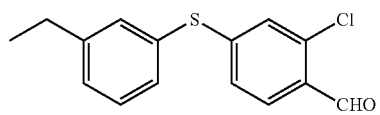

3-Ethylbenzenethiol and 2-chloro-4-fluorobenzaldehyde were reacted according to the same experiment procedures as in Reference Example 1 of the pamphlet of WO 03029205 to obtain the target product as a colorless oil.
$^1$H-NMR (CDCl$_3$, 400 MHz): δ 1.26 (3H, t, J=7.3 Hz), 2.68 (2H, q, J=7.3 Hz), 7.04-7.11 (2H, m), 7.28-7.40 (4H, m), 7.76 (1H, d, J=8.6 Hz), 10.35 (1H, s).
EIMS (+): 276 [M]$^+$.

Reference Example 5

2-Chloro-4-(3-propylphenoxy)benzaldehyde

[Chemical formula 21]

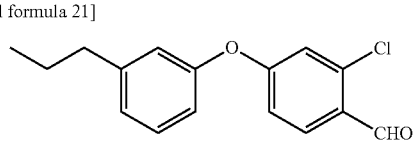

3-Propylphenol and 2-chloro-4-fluorobenzaldehyde were reacted according to the same experiment procedures as in Reference Example 1 of the pamphlet of WO 03029184 to obtain the target product as a pale brown oil.
$^1$H-NMR (CDCl$_3$, 400 MHz): δ 0.95 (3H, t, J=7.3 Hz), 1.62-1.68 (2H, m), 2.61 (2H, t, J=7.3 Hz), 6.89-6.94 (3H, m), 6.96 (1H, d, J=2.1 Hz), 7.08 (1H, d, J=7.9 Hz), 7.31-7.35 (1H, m), 7.90 (1H, d, J=8.9 Hz), 10.36 (1H, d, J=0.6 Hz).
EIMS(+): 274 [M]$^+$.

Reference Example 6

[2-Chloro-4-(3-ethylphenylthio)phenyl]acetaldehyde

[Chemical formula 22]

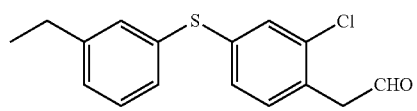

The compound of Reference Example 4 was reacted according to the same experiment procedures as in Reference Example 326 of the pamphlet of WO 04074297 to obtain the target product as a pale yellow oil.

Reference Example 7

Ethyl 3-[2-chloro-4-(3-ethylphenylthio)phenyl]acrylate

[Chemical formula 23]

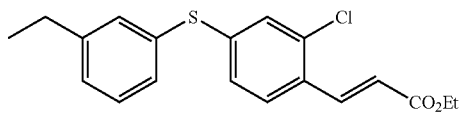

The compound of Reference Example 4 was reacted according to the same experiment procedures as in Reference Example 10 of the pamphlet of WO 03029205 to obtain the target product as a pale yellow oil.
EIMS(+): 346 [M]$^+$.

Reference Example 8

3-[2-Chloro-4-(3-ethylphenylthio)phenyl]propan-1-ol

[Chemical formula 24]

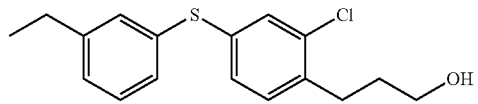

The compound of Reference Example 7 was reacted according to the same experiment procedures as in Reference Example 19 of the pamphlet of WO 03029205, and the resultant product was then reduced according to the same experiment procedures as in Reference Example 35 of the pamphlet of WO 03029205, to obtain the target product as a colorless oil.
$^1$H-NMR (CDCl$_3$, 400 MHz,): δ 1.22 (3H, t, J=7.3 Hz), 1.84-1.90 (2H, m), 2.62 (2H, q, J=7.6 Hz), 2.78-2.82 (2H, m), 3.69 (2H, t, J=6.1 Hz), 7.10-7.18 (4H, m), 7.23-7.29 (3H, m).

Reference Example 9

3-[2-Chloro-4-(3-propylphenoxy)phenyl]propan-1-ol

[Chemical formula 25]

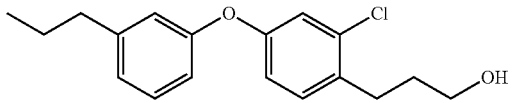

The compound of Reference Example 5 was successively reacted according to the same procedures as in Reference Example 7 and then Reference Example 8 to obtain the target product as a colorless oil.
$^1$H-NMR (CDCl$_3$, 400 MHz,): δ 0.94 (3H, t, J=7.3 Hz), 1.37 (1H, br s), 1.58-1.68 (2H, m), 1.85-1.92 (2H, m), 2.57 (2H, t, J=7.6 Hz), 2.80 (2H, t, J=7.6 Hz), 3.70 (2H, dt, J=6.1, 4.6 Hz), 6.80-6.85 (3H, m), 6.95 (1H, d, J=7.9 Hz), 7.00 (1H, d, J=2.8 Hz), 7.17 (1H, d, J=8.3 Hz), 7.24 (1H, t, J=7.9 Hz).
EIMS(+): 304 [M]$^+$.

Reference Example 10

3-[2-Fluoro-4-(3-trifluoromethylphenylthio)phenyl]propan-1-ol

[Chemical formula 26]

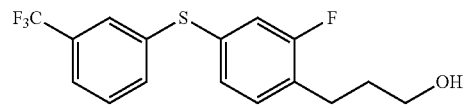

The compound of Reference Example 1 was successively reacted according to the same procedures as in Reference Example 7 and then Reference Example 8 to obtain the target product as a colorless oil.
$^1$H-NMR (CDCl$_3$, 400 MHz): δ 1.88 (2H, tt, J=6.7, 6.1 Hz), 2.75 (2H, t, J=6.7 Hz), 3.69 (2H, t, J=6.1 Hz), 7.05 (1H, dd, J=10, 1.8 Hz), 7.10 (1H, dd, J=7.9, 1.8 Hz), 7.20 (1H, t, J=7.9 Hz), 7.38-7.51 (3H, m), 7.55 (1H, s).

Reference Example 11

3-[2-Chloro-4-(3-chlorophenylthio)phenyl]propan-1-ol

[Chemical formula 27]

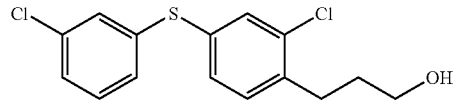

The compound of Reference Example 2 was successively reacted according to the same procedures as in Reference Example 7 and then Reference Example 8 to obtain the target product as a colorless oil.
$^1$H-NMR (CDCl$_3$, 400 MHz): δ 1.33 (1H, brs), 1.83-1.95 (2H, m), 2.81-2.85 (2H, m), 3.70 (2H, br s), 7.15-7.23 (5H, m), 7.24-7.29 (1H, m), 7.38 (1H, d, J=1.8 Hz).

Reference Example 12

3-[2-Chloro-4-(3-methylphenoxy)phenyl]propan-1-ol

[Chemical formula 28]

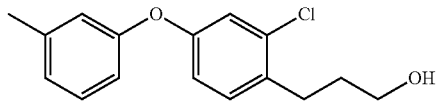

The compound of Reference Example 3 was successively reacted according to the same procedures as in Reference Example 7 and then Reference Example 8 to obtain the target product as a colorless oil.
$^1$H-NMR (CDCl$_3$, 400 MHz): δ 1.31 (1H, brs), 1.87-1.90 (2H, m), 2.34 (3H, s), 2.80 (2H, t, J=7.3 Hz), 3.70 (2H, dd, J=11.6, 6.1 Hz), 6.79-6.86 (3H, m), 6.94 (1H, d, J=7.3 Hz), 6.99 (1H, d, J=2.4 Hz), 7.18 (1H, d, J=7.9 Hz), 7.22 (1H, t, J=7.3 Hz).
EIMS (+): 276 [M]⁺.

Reference Example 13

2-Chloro-4-(3-ethylphenylthio)-1-(2-iodoethyl)benzene

[Chemical formula 29]

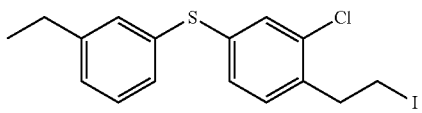

The compound of Reference Example 6 was reacted according to the same experiment procedures as in Reference Example 327 of the pamphlet of WO 04074297 to obtain the target product as a colorless oil.
¹H-NMR (CDCl₃, 400 MHz): δ 1.22 (3H, t, J=7.3 Hz), 2.63 (2H, q, J=7.3 Hz), 3.23-3.28 (2H, m), 3.32-3.35 (2H, m), 7.09-7.29 (7H, m).
EIMS (+): 402 [M]⁺.

Reference Example 14

2-Chloro-4-(3-ethylphenylthio)-1-(3-iodopropyl)benzene

[Chemical formula 30]

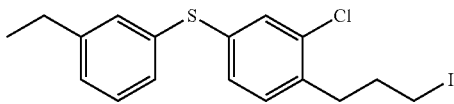

The compound of Reference Example 8 was reacted according to the same experiment procedures as in Reference Example 164 of the pamphlet of WO 03029184 to obtain the target product as a colorless oil.
¹H-NMR (CDCl₃, 400 MHz): δ 1.22 (3H, t, J=7.3 Hz), 2.12 (2H, quintet, J=7.3 Hz), 2.63 (2H, q, J=7.3 Hz), 2.81(2H, t, J=7.3 Hz), 3.19 (2H, t, J=7.3 Hz), 7.09-7.19 (4H, m), 7.24-7.28 (3H, m).
EIMS (+): 416 [M]⁺.

Reference Example 15

2-Chloro-1-(3-iodopropyl)-4-(3-propylphenoxy)benzene

[Chemical formula 31]

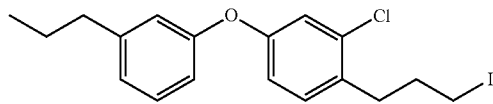

The compound of Reference Example 9 was reacted according to the same experiment procedures as in Reference Example 164 of the pamphlet of WO 03029184 to obtain the target product as a pale yellow oil.
¹H-NMR (CDCl₃, 400 MHz): δ 0.94 (3H, t, J=7.3 Hz), 1.60-1.68 (2H, m), 2.10-2.17 (2H, m), 2.57 (2H, t, J=7.6 Hz), 2.81 (2H, t, J=7.6 Hz), 3.21 (2H, t, J=7.0 Hz), 6.80-6.85 (3H, m), 6.96 (1H, d, J=7.9 Hz), 6.99 (1H, d, J=2.4 Hz), 7.19 (1H, d, J=8.3 Hz), 7.25 (1H, t, J=7.9 Hz).
EIMS(+): 414 [M]⁺.

Reference Example 16

2-Fluoro-1-(3-iodopropyl)-4-(3-trifluoromethylphenylthio)benzene

[Chemical formula 32]

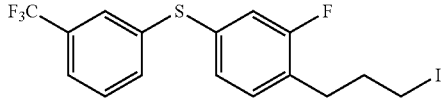

The compound of Reference Example 10 was reacted according to the same experiment procedures as in Reference Example 164 of the pamphlet of WO 03029184 to obtain the target product as a colorless oil.
¹H-NMR (CDCl₃, 400 MHz): δ 2.13 (2H, quintet, J=7.3 Hz), 2.76 (2H, t, J=7.3 Hz), 3.18 (2H, t, J=6.7 Hz), 7.03 (1H, dd, J=10, 1.8 Hz), 7.09(1H, dd, J=7.9, 1.8 Hz), 7.20 (1H, t, J=7.9 Hz), 7.39-7.52 (3H, m), 7.57 (1H, s).
EIMS(+): 404 [M]⁺.

Reference Example 17

2-Chloro-4-(3-chlorophenylthio)-1-(3-iodopropyl)benzene

[Chemical formula 33]

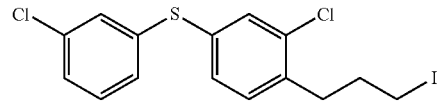

The compound of Reference Example 11 was reacted according to the same experiment procedures as in Reference Example 164 of the pamphlet of WO 03029184 to obtain the target product as a colorless oil.
¹H-NMR (CDCl₃, 400 MHz): δ 2.14 (2H, tt, J=7.3, 6.7 Hz), 2.84 (2H, t, J=7.3 Hz), 3.20 (2H, t, J=6.7 Hz), 7.16-7.25 (5H, m), 7.28 (1H, t, J=1.8 Hz), 7.36 (1H, d, J=1.8 Hz).
EIMS (+): 422 [M]⁺.

Reference Example 18

2-Chloro-1-(3-iodopropyl)-4-(3-methylphenoxy)benzene

[Chemical formula 34]

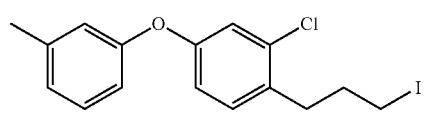

The compound of Reference Example 12 was reacted according to the same experiment procedures as in Reference Example 164 of the pamphlet of WO 03029184 to obtain the target product as a yellow oil.

¹H-NMR (CDCl₃, 400 MHz): δ 2.13 (2H, quint, J=7.3 Hz), 2.34 (3H, s), 2.81 (2H, t, J=7.3 Hz), 3.21 (2H, t, J=7.3 Hz), 6.81-6.84 (3H, m), 6.95 (1H, d, J=7.9 Hz), 6.99 (1H, d, J=2.4 Hz), 7.18 (1H, d, J=7.9 Hz), 7.23 (1H, t, J=7.9 Hz).
EIMS (+): 386 [M]⁺.

Example 1

(2R,5S)-2-[2-chloro-4-(3-trifluoromethylphenoxy)phenyl]propyl-3,6-diethoxy-5-isopropyl-2-methyl-2,5-dihydropyrazine

[Chemical formula 35]

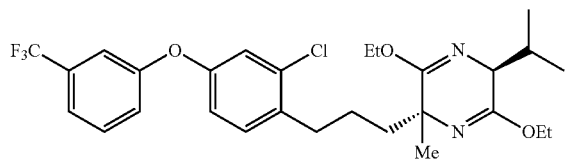

Under an argon atmosphere, a solution of n-butyllithium in hexane (1.54 mol/L, 3.59 mL) was added at −78° C. into a solution of (5S)-3,6-diethoxy-5-isopropyl-2-methyl-2,5-dihydropyrazine (905 mg) in THF (16 mL), and the resultant solution was stirred at −78° C. for 30 minutes. Next, A solution of 2-chloro-1-(3-iodopropyl)-4-(3-trifluoromethylphenoxy)benzene (2.47 g) in THF (4 mL) was added to the reaction mixture, and the resultant solution was stirred at −78° C. for 30 minutes and then at 0° C. for 1 hour. To the reaction solution was added water, extracted with ethyl acetate, washed with water and saturated brine in that order, and then dried over anhydrous sodium sulfate. The solvent was evaporated, and the resultant residue was purified by silica gel column chromatography (hexane:ethyl acetate=60:1) to obtain the target product (1.59 g) as a colorless oil.
¹H-NMR (CDCl₃, 400 MHz): δ 0.70 (3H, d, J=6.7 Hz), 1.05 (3H, d, J=6.7 Hz), 1.18-1.50 (9H, m), 1.32 (3H, s), 1.86-1.97 (1H, m), 2.21-2.30 (1H, m), 2.65 (2H, t, J=7.6 Hz), 3.90 (1H, d, J=2.1 Hz), 3.97-4.21 (4H, m), 6.84 (1H, dd, J=7.9, 2.4 Hz), 7.00 (1H, d, J=2.4 Hz), 7.15 (2H, d, J=7.9 Hz), 7.24 (1H, br s), 7.36 (1H, d, J=7.9 Hz), 7.44 (1H, t, J=7.9 Hz).

Example 2

(2R,5S)-2-[2-chloro-4-(3-trifluoromethylphenylthio)phenyl]propyl-3,6-diethoxy-5-isopropyl-2-methyl-2,5-dihydropyrazine

[Chemical formula 36]

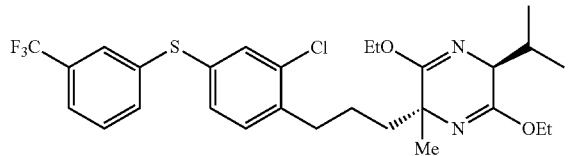

(5S)-3,6-diethoxy-5-isopropyl-2-methyl-2,5-dihydropyrazine and 2-chloro-1-(3-iodopropyl)-4-(3-trifluoromethylphenylthio)benzene were reacted in the same manner as in Example 1 to obtain the target product as a colorless oil.
¹H-NMR (CDCl₃, 400 MHz): δ 0.63 (3H, d, J=6.7 Hz), 1.07 (3H, d, J=6.7 Hz), 1.18-1.29 (10H, m), 1.34-1.66 (2H, m), 1.79-1.91 (1H, m), 2.25-2.33 (1H, m), 2.70 (2H, t, J=7.6 Hz), 3.85 (1H, br s), 3.99-4.23 (4H, m), 7.16 (2H, d, J=7.9 Hz), 7.20 (1H, dd, J=7.9, 1.8 Hz), 7.36-7.42 (3H, m), 7.44-7.50 (1H, m), 7.52 (1H, br s).

Example 3

(2R,5S)-2-[2-chloro-4-(3-trifluoromethylphenoxy)phenyl]ethyl-3,6-diethoxy-5-isopropyl-2-methyl-2,5-dihydropyrazine

[Chemical formula 37]

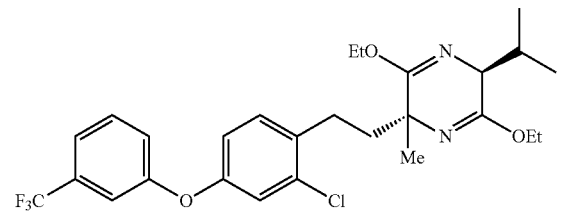

(5S)-3,6-diethoxy-5-isopropyl-2-methyl-2,5-dihydropyrazine and 2-chloro-1-(2-iodoethyl)-4-(3-trifluoromethylphenoxy)benzene were reacted in the same manner as in Example 1 to obtain the target product as a colorless oil.
¹H-NMR (CDCl₃, 400 MHz): δ 0.72 (3H, d, J=6.7 Hz), 1.08 (3H, d, J=6.7 Hz), 1.29 (6H, t, J=7.3 Hz), 1.36 (3H, s), 1.74-1.82 (1H, m), 2.13-2.20 (1H, m), 2.25-2.32 (1H, m), 2.39-2.56 (2H, m), 3.95 (1H, d, J=3.1 Hz), 4.02-4.22 (4H, m), 6.83 (1H, dd, J=8.6, 2.4 Hz), 6.99 (1H, d, J=2.4 Hz), 7.12-7.15 (2H, m), 7.23 (1H, br s), 7.35 (1H, d, J=7.8 Hz), 7.44 (1H, t, J=7.8 Hz).
EIMS (+): 524 [M]⁺.

Example 4

(2R,5S)-2-[2-chloro-4-(3-trifluoromethylphenylthio)phenyl]ethyl-3,6-diethoxy-5-isopropyl-2-methyl-2,5-dihydropyrazine

[Chemical formula 38]

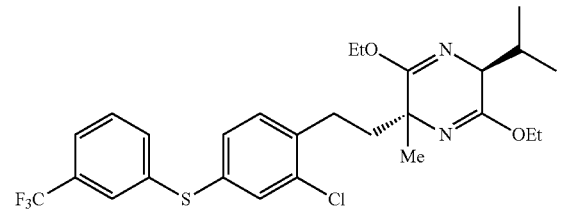

(5S)-3,6-diethoxy-5-isopropyl-2-methyl-2,5-dihydropyrazine and 2-chloro-1-(2-iodoethyl)-4-(3-trifluoromethylphenylthio)benzene were reacted in the same manner as in Example 1 to obtain the target product as a colorless oil.
¹H-NMR (CDCl₃, 400 MHz): δ 0.72 (3H, d, J=6.7 Hz), 1.08 (3H, d, J=6.7 Hz), 1.28 (6H, t, J=7.3 Hz), 1.35 (3H, s), 1.68-1.90 (1H, m), 2.10-2.19 (1H, m), 2.38-2.57 (1H, m), 3.95 (1H, d, J=3.1 Hz), 4.02-4.22 (4H, m), 7.13 (1H, d, J=7.9 Hz), 7.18 (1H, dd, J=7.9, 2.4 Hz), 7.35-7.42 (3H, m), 7.43-7.48 (1H, m), 7.54 (1H, br s).

Example 5

(2R,5S)-2-[2-chloro-4-(3-ethylphenylthio)phenyl]ethyl-3,6-diethoxy-5-isopropyl-2-methyl-2,5-dihydropyrazine

[Chemical formula 39]

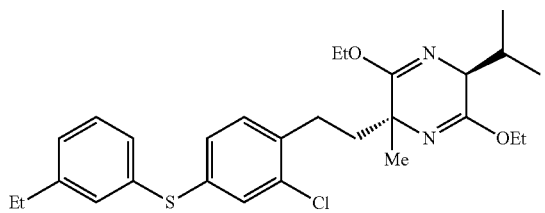

(5S)-3,6-diethoxy-5-isopropyl-2-methyl-2,5-dihydropyrazine and the compound of Reference Example 13 were reacted in the same manner as in Example 1 to obtain the target product as a colorless oil.

$^1$H-NMR(CDCl$_3$, 400 MHz): δ 0.72 (3H, d, J=6.7 Hz), 1.07 (3H, d, J=6.7 Hz), 1.21 (3H, t, J=7.3 Hz), 1.28 (3H, t, J=7.3 Hz), 1.29 (3H, t, J=7.3 Hz), 1.34 (3H, s), 1.70-1.79 (1H, m), 2.09-2.16 (1H, m), 2.24-2.32 (1H, m), 2.35-2.52 (2H, m), 2.61 (2H, q, J=7.3 Hz), 3.95 (1H, d, J=3.1 Hz), 4.03-4.20 (4H, m), 7.04-7.15 (4H, m), 7.21-7.26 (3H, m).

ESIMS (+): 501 [M+H]$^+$.

Example 6

(2R,5S)-2-[2-chloro-4-(3-methylphenoxy)phenyl]propyl-3,6-dimethoxy-5-isopropyl-2-methyl-2,5-dihydropyrazine

[Chemical formula 40]

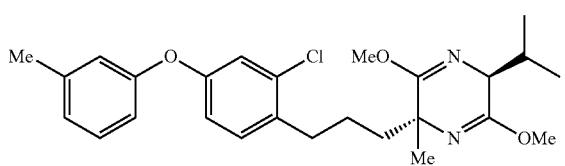

(5S)-3,6-dimethoxy-5-isopropyl-2-methyl-2,5-dihydropyrazine and the compound of Reference Example 18 were reacted in the same manner as in Example 1 to obtain the target product as a colorless oil.

$^1$H-NMR (CDCl$_3$, 400 MHz): δ 0.68 (3H, d, J=6.7 Hz), 1.07 (3H, d, J=6.7 Hz), 1.33 (3H, s), 1.36-1.43 (1H, m), 1.55-1.62 (1H, m), 1.86-1.92 (1H, m), 2.24-2.26 (1H, m), 2.34 (3H, s), 2.62 (2H, t, J=7.9 Hz), 3.65 (3H, s), 3.66 (3H, s), 3.94 (1H, d, J=3.7 Hz), 6.79-6.82 (3H, m), 6.93 (1H, d, J=7.3 Hz), 6.96 (1H, d, J=2.4 Hz), 7.09 (1H, d, J=7.9 Hz), 7.22 (1H, t, J=7.9 Hz).

EIMS (+): 456 [M]$^+$.

Example 7

(2R,5S)-2-[2-chloro-4-(3-ethylphenylthio)phenyl]propyl-3,6-diethoxy-5-isopropyl-2-methyl-2,5-dihydropyrazine

[Chemical formula 41]

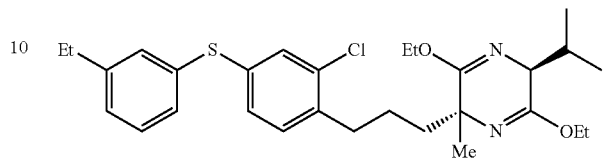

(5S)-3,6-diethoxy-5-isopropyl-2-methyl-2,5-dihydropyrazine and the compound of Reference Example 14 were reacted in the same manner as in Example 1 to obtain the target product as a colorless oil.

$^1$H-NMR (CDCl$_3$, 400 MHz): δ 0.68 (3H, d, J=6.7 Hz), 1.04 (3H, d, J=6.7 Hz), 1.20-1.26 (9H, m), 1.31 (3H, s), 1.36-1.43 (1H, m), 1.50-1.57 (1H, m), 1.85-1.92 (1H, m), 2.21-2.28 (1H, m), 2.60-2.65 (4H, m), 3.88 (1H, d, J=3.7 Hz), 4.00-4.16 (4H, m), 7.06-7.16 (4H, m), 7.22-7.27 (3H, m).

ESIMS (+): 515 [M+H]$^+$.

Example 8

(2R,5S)-2-[2-chloro-4-(3-chlorophenylthio)phenyl]propyl-3,6-diethoxy-5-isopropyl-2-methyl-2,5-dihydropyrazine

[Chemical formula 42]

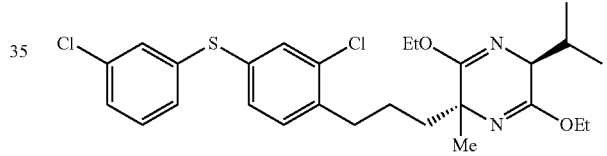

(5S)-3,6-diethoxy-5-isopropyl-2-methyl-2,5-dihydropyrazine and the compound of Reference Example 17 were reacted in the same manner as in Example 1 to obtain the target product as a colorless oil.

$^1$H-NMR (CDCl$_3$, 400 MHz): δ 0.69 (3H, d, J=6.7 Hz), 1.08 (3H, d, J=6.7 Hz), 1.18-1.29 (7H, m), 1.31 (3H, s), 1.34-1.47 (1H, m), 1.50-1.63 (1H, m), 1.85-1.95 (1H, m), 2.20-2.30 (1H, m), 2.65 (2H, t, J=7.6 Hz), 3.89 (1H, d, J=3.1 Hz), 3.99-4.23 (4H, m), 7.11-7.23 (6H, m), 7.35 (1H, d, J=1.8 Hz).

ESIMS (+): 521 [M+H]$^+$.

Example 9

(2R,5S)-2-[2-fluoro-4-(3-trifluoromethylphenylthio)phenyl]propyl-3,6-diethoxy-5-isopropyl-2-methyl-2,5-dihydropyrazine

[Chemical formula 43]

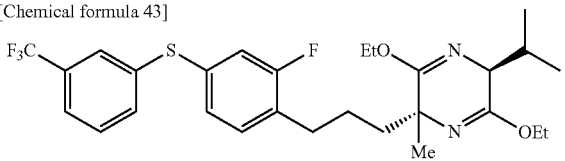

(5S)-3,6-diethoxy-5-isopropyl-2-methyl-2,5-dihydropyrazine and the compound of Reference Example 16 were reacted in the same manner as in Example 1 to obtain the target product as a colorless oil.

$^1$H-NMR (CDCl$_3$, 400 MHz): δ 0.67 (3H, d, J=6.7 Hz), 1.06(3H, d, J=6.7 Hz), 1.18-1.29 (7H, m), 1.33 (3H, s), 1.36-1.66 (2H, m), 1.85-1.95 (1H, m), 2.23-2.33 (1H, m), 2.67 (2H, t, J=7.6 Hz), 3.89 (1H, d, J=3.1 Hz), 3.99-4.23 (4H, m), 7.02 (1H, dd, J=9.8 Hz, 1.8 Hz), 7.08 (1H, dd, J=7.9 Hz, 2.4 Hz), 7.13 (1H, t, J=7.9 Hz), 7.38-7.50 (3H, m), 7.55 (1H, s).

Example 10

(2S,5S)-2-allyl-2-[2-chloro-4-(3-trifluoromethylphenylthio)phenyl]propyl-3,6-diethoxy-5-isopropyl-2,5-dihydropyrazine

[Chemical formula 44]

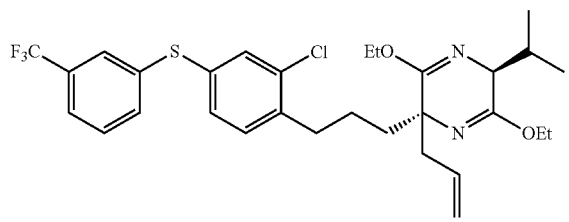

(5S)-2-allyl-3,6-diethoxy-5-isopropyl-2,5-dihydropyrazine and 2-chloro-1-(3-iodopropyl)-4-(3-trifluoromethylphenylthio)benzene were reacted in the same manner as in Example 1 to obtain the target product as a colorless oil.

$^1$H-NMR (CDCl$_3$, 400 MHz): δ 0.67 (3H, d, J=6.7 Hz), 1.05 (3H, d, J=6.7 Hz), 1.23 (3H, t, J=6.4 Hz), 1.25 (3H, t, J=6.4 Hz), 1.30-1.64 (3H, m), 1.80-1.90 (1H, m), 2.23-2.39 (2H, m), 2.53 (1H, dd, J=12.4, 7.3 Hz), 2.65 (2H, t, J=7.6 Hz), 3.83 (1H, d, J=3.1 Hz), 4.03-4.18 (4H, m), 4.92-5.04 (2H, m), 5.60-5.73 (1H, m), 7.13 (2H, d, J=7.9 Hz), 7.18 (1H, dd, J=7.9 Hz, 1.8 Hz), 7.36 (1H, d, J=1.8 Hz), 7.38-7.42 (2H, m), 7.44-7.49 (1H, m), 7.55 (1H, br s).

Example 11

Ethyl (R)-2-t-butoxycarbonylamino-5-[2-chloro-4-(3-trifluoromethylphenoxy)phenyl]-2-methylpentanoate

[Chemical formula 45]

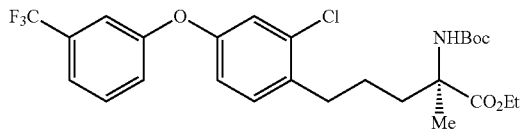

To a solution of the compound of Example 1 (1.59 g) in 1,4-dioxane (60 mL) was added 0.5 mol/L hydrochloric acid (30 mL). The resultant solution was stirred at room temperature for 1 hour, and then left to stand at room temperature overnight. The solution was concentrated, neutralized with saturated aqueous sodium hydrogen carbonate solution, and extracted with ethyl acetate. The extract was washed with water and saturated brine, and then dried over anhydrous sodium sulfate. The extract was concentrated, and the resultant residue was dissolved in acetonitrile (15 mL). To this solution was added di-tert-butoxydicarbonate (1.55 g), and the resultant solution was stirred at room temperature for 4 hours and then left to stand at room temperature overnight. To the reaction solution added water, extracted with ethyl acetate, washed with water and saturated brine in that order, and then dried over anhydrous sodium sulfate. The solvent was evaporated, and the resultant residue was purified by silica gel column chromatography (hexane ethyl acetate=9:1) to obtain the target product (1.00 g) as a colorless oil.

$^1$H-NMR (CDCl$_3$, 400 MHz): δ 1.26 (3H, t, J=7.3 Hz), 1.43 (9H, s), 1.53 (3H, s), 1.45-1.68 (2H, m), 1.80-1.90 (1H, m), 2.12-2.30 (1H, m), 2.69 (2H, t, J=7.6 Hz), 4.16-4.24 (2H, m), 5.33 (1H, br s), 6.85 (1H, dd, J=7.9 Hz, 2.4 Hz), 7.02 (1H, d, J=2.4 Hz), 7.15 (1H, dd, J=7.9 Hz, 2.4 Hz), 7.17 (1H, d, J=7.9 Hz), 7.24 (1H, br s), 7.37 (1H, d, J=7.9 Hz), 7.45 (1H, t, J=7.9 Hz).

Example 12

Ethyl (R)-2-t-butoxycarbonylamino-5-[2-fluoro-4-(3-trifluoromethylphenylthio)phenyl]-2-methylpentanoate

[Chemical formula 46]

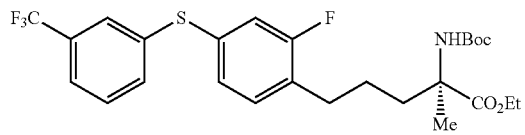

The compound of Example 9 was reacted in the same manner as in Example 11 to obtain the target product as a colorless oil.

$^1$H-NMR (CDCl$_3$, 400 MHz): δ 1.26 (3H, t, J=7.3 Hz), 1.42 (9H, s), 1.51 (3H, s), 1.45-1.68 (2H, m), 1.77-1.86 (1H, m), 2.09-2.20 (1H, m), 2.69 (2H, t, J=7.6 Hz), 4.13-4.23 (2H, m), 5.29 (1H, br s), 7.02 (1H, dd, J=9.8 Hz, 1.8 Hz), 7.08 (1H, dd, J=7.9 Hz, 2.4 Hz), 7.13 (1H, t, J=7.9 Hz), 7.38-7.50 (3H, m), 7.55 (1H, s).

Example 13

Ethyl (S)-2-allyl-2-t-butoxycarbonylamino-5-[2-chloro-4-(3-trifluoromethylphenylthio)phenyl]pentanoate

[Chemical formula 47]

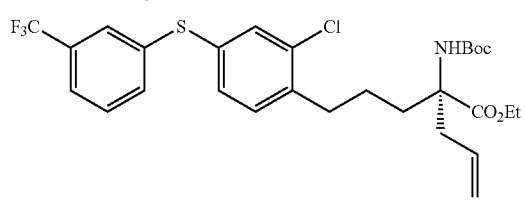

The compound of Example 10 was reacted in the same manner as in Example 11 to obtain the target product as a colorless oil.

¹H-NMR (CDCl₃, 400 MHz) δ 1.24 (3H, t, J=7.3 Hz), 1.29-1.39 (1H, m), 1.43 (9H, s), 1.60-1.70 (1H, m), 1.78-1.86 (1H, m), 2.32-2.50 (2H, m), 2.66-2.73 (2H, m), 2.99-3.10 (1H, m), 4.19 (2H, q), 5.03 (1H, d, J=3.1 Hz), 5.09 (1H,. s), 5.49 (1H, br s), 5.54-5.68 (1H, m), 7.16 (1H, d, J=7.9 Hz), 7.19 (1H, dd, J=7.9, 1.8 Hz), 7.35 (1H, d, J=1.8 Hz), 7.39-7.44 (2H, m), 7.45-7.50 (1H, m), 7.54 (1H, br s).

Example 14

Ethyl (R)-2-t-butoxycarbonylamino-5-[2-chloro-4-(3-trifluoromethylphenylthio)phenyl]-2-propylpentanoate

[Chemical formula 47]

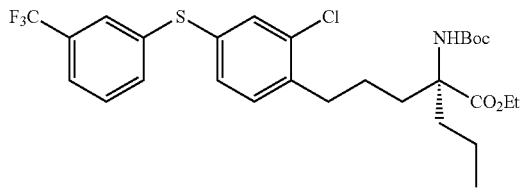

To a solution of the compound of Example 13 (400 mg) in ethyl acetate (20 mL) was added palladium, on activated carbon/ethylene diamine complex (100 mg), and the resultant solution was stirred at room temperature for 24 hours under hydrogen atmosphere. The reaction solution was filtered through Celite, and the solvent was evaporated. The resultant residue was purified by silica gel column chromatography (hexane:ethyl acetate=30:1) to obtain the target product (293 mg) as a colorless oil.

¹H-NMR (CDCl₃, 400 MHz): δ 0.91 (3H, t, J=7.3 Hz), 1.42 (9H, s), 1.15-1.77 (8H, m), 2.72 (2H, t, J=7.3 Hz), 3.63 (1H, d, J=12 Hz), 3.67 (1H, d, J=12 Hz), 4.52 (1H, br s), 7.19-7.22 (2H, m), 7.39 (1H, s), 7.40-7.50 (3H, m), 7.54 (1H, br s).

FABMS (+): 532 [M+H]⁺.

Example 15

(R)-2-t-butoxycarbonylamino-5-[2-chloro-4-(3-trifluoromethylphenoxy)phenyl]-2-methylpentan-1-ol

[Chemical formula 49]

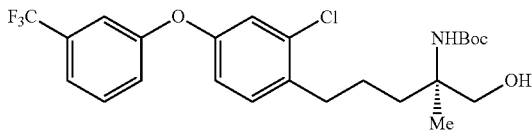

To a solution of the compound of Example 11 (1.00 g) in THF (14 mL) was added under ice cooling lithium borohydride (229 mg), and then ethanol (1.4 mL) was added dropwise. The resultant solution was then stirred for 1 hour under ice cooling. To the reaction solution was added 10% aqueous citric acid, extracted with ethyl acetate, washed with water and saturated brine in that order, and then dried over anhydrous sodium sulfate. The solvent was evaporated, and the resultant residue was purified by silica gel column chromatography (hexane:ethyl acetate=4:1) to obtain the target product (910 mg) as a colorless oil.

¹H-NMR (CDCl₃, 400 MHz): δ 1.16 (3H, s), 1.43 (9H, s), 1.53-1.74 (3H, m), 1.81-1.93 (1H, m), 2.73 (2H, t, J=7.3 Hz), 3.61 (1H, d, J=12 Hz), 3.65 (1H, d, J=12 Hz), 4.58 (1H, br s), 4.58 (1H, br s), 6.86 (1H, dd, J=7.9, 2.4 Hz), 7.03 (1H, d, J=2.4 Hz), 7.16 (1H, dd, J=7.9 Hz, 2.4 Hz), 7.21 (1H, d, J=7.9 Hz), 7.24 (1H, br s), 7.37 (1H, d, J=7.9 Hz), 7.45 (1H, t, J=7.9 Hz).

Example 16

(R)-2-t-butoxycarbonylamino-5-[2-chloro-4-(3-trifluoromethylphenylthio)phenyl]-2-methylpentan-1-ol

[Chemical formula 50]

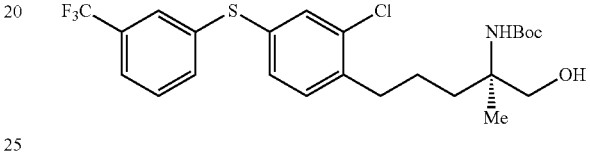

The compound of Example 2 was reacted in the same manner as in Example 11 to obtain an ester, which was then reacted in the same manner as in Example 15 to obtain the target product as a colorless oil.

¹H-NMR (CDCl₃, 400 MHz): δ 1.14 (3H, s), 1.42 (9H, s), 1.48-1.76 (4H, m), 1.81-1.90 (1H, m), 2.74 (2H, t, J=6.7 Hz), 3.61 (1H, d, J=12 Hz), 3.65 (1H, d, J=12 Hz), 4.56 (1H, br s), 4.58 (1H, br s), 7.20 (2H, d, J=1.2 Hz), 7.37-7.50 (4H, m), 7.54 (1H, br s).

Optical Rotation: $[\alpha]_D^{27}$ +14.31 (c 0.63, CHCl₃).

Example 17

(R)-2-t-butoxycarbonylamino-4-[2-chloro-4-(3-trifluoromethylphenoxy)phenyl]-2-methylbutan-1-ol

[Chemical formula 51]

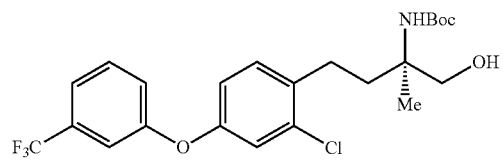

The compound of Example 3 was reacted in the same manner as in Example 11 to obtain an ester, which was then reacted in the same manner as in Example 15 to obtain the target product as a colorless oil.

¹H-NMR (CDCl₃, 400 MHz): δ 1.26 (3H, s), 1.45 (9H, s), 1.80-1.88 (1H, m), 2.05-2.12 (1H, m), 2.66-2.80 (2H, m), 3.68 (1H, d, J=11.6 Hz), 3.73 (1H, d, J=11.6 Hz), 4.70 (1H, br s), 6.86 (1H, dd, J=8.5, 2.5 Hz), 7.03 (1H, d, J=2.5 Hz), 7.13-7.16 (1H, m), 7.22-7.24 (2H, m), 7.37 (1H, d, J=7.9 Hz), 7.45 (1H, t, J=7.9 Hz).

FABMS (+): 474 [M+H]⁺.

Example 18

(R)-2-t-butoxycarbonylamino-4-[2-chloro-4-(3-trifluoromethylphenylthio)phenyl]-2-methylbutan-1-ol

[Chemical formula 52]

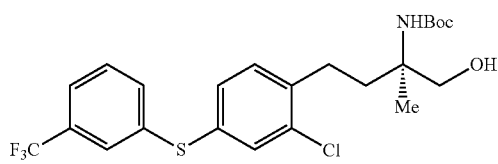

The compound of Example 4 was reacted in the same manner as in Example 11 to obtain an ester, which was then reacted in the samemanneras in Example 15 to obtain the targetproduct asacolorless oil.

$^1$H-NMR (CDCl$_3$, 400 MHz): δ 1.25 (3H, s), 1.44 (9H, s), 1.79-1.89 (1H, m), 2.05-2.13 (1H, m), 2.66-2.83 (2H, m), 3.68 (1H, d, J=12 Hz), 3.71 (1H, d, J=12 Hz), 4.69 (1H, br s), 7.20-7.23 (2H, m), 7.37-7.42 (3H, m), 7.45-7.50 (2H, m), 7.55 (1H, br s).

Example 19

(R)-2-t-butoxycarbonylamino-4-[2-chloro-4-(3-ethylphenylthio)phenyl]-2-methylbutan-1-ol

[Chemical formula 53]

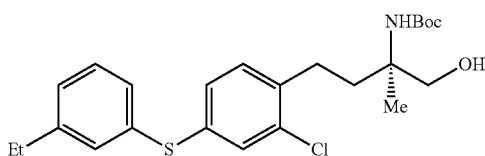

The compound of Example 5 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.22 (3H, t, J=7.3 Hz), 1.24 (3H, s), 1.44 (9H, s), 1.77-1.85 (1H, m), 2.02-2.09 (1H, m), 2.62(2H, q, J=7.3 Hz), 2.63-2.78 (2H, m), 3.64-3.73 (2H, m), 4.08 (1H, br), 4.68 (1H, br s), 7.10-7.17 (4H, m), 7.22-7.28 (3H, m).

ESIMS (+): 450 [M+H]$^+$.

Example 20

(R)-2-t-butoxycarbonylamino-5-[2-chloro-4-(3-methylphenoxy)phenyl]-2-methylpentan-1-ol

[Chemical formula 54]

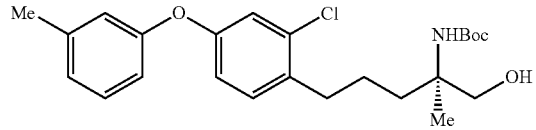

The compound of Example 6 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.15 (3H, s), 1.43 (9H, s), 1.61-1.67 (3H, m), 1.83-1.87 (1H, m), 2.34 (3H, s), 2.70 (2H, t, J=7.0 Hz), 3.62-3.65 (2H, m), 4.57 (1H, s), 6.81-6.84 (3H, m), 6.94 (1H, d, J=7.3 Hz), 6.98 (1H, d, J=3.1 Hz), 7.15 (1H, d, J=7.9 Hz), 7.22 (1H, t, J=7.9 Hz).

ESIMS (+): 434 [M+H]$^+$.

Example 21

(R)-2-t-butoxycarbonylamino-5-[2-chloro-4-(3-ethylphenylthio)phenyl]-2-methylpentan-1-ol

[Chemical formula 55]

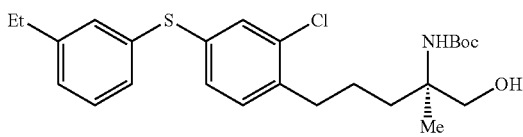

The compound of Example 7 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.14 (3H, s), 1.22 (3H, t, J=7.3 Hz), 1.43 (9H, s), 1.54-1.70 (3H, m), 1.79-1.89 (1H, m), 2.62 (2H, q, J=7.3 Hz), 2.70 (2H, t, J=7.0 Hz), 3.57-3.66 (2H, m), 4.05 (1H, br), 4.55 (1H, br s), 7.10-7.17 (4H, m), 7.17-7.28 (3H, m).

ESIMS (+): 464 [M+H]$^+$.

Example 22

(R)-2-t-butoxycarbonylamino-5-[2-chloro-4-(3-propylphenoxy)phenyl]-2-methylpentan-1-ol

[Chemical formula 56]

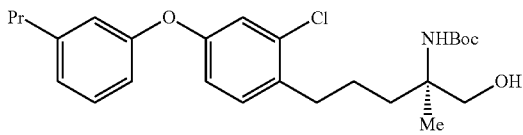

The compound of Reference Example 15 and (5S)-3,6-diethoxy-5-isopropyl-2-methyl-2,5-dihydropyrazine were reacted with in the same manner as in Example 1. The resultant compound was reacted in the same manner as in Example 11 to obtain an ester, which was then reacted in the same manner as in Example 15 to obtain the target product as a colorless oil.

$^1$H-NMR (CDCl$_3$, 400 MHz): δ 0.94 (3H, t, J=7.3 Hz), 1.15 (3H, s), 1.24-1.28 (2H, m), 1.43 (9H, s), 1.60-1.69 (3H, m), 1.80-1.90 (1H, m), 2.57 (2H, t, J=7.6 Hz), 2.70 (2H, t, J=7.6 Hz), 3.58-3.67 (2H, m), 4.11 (1H, br s), 4.58 (1H, br s), 6.79-6.85 (3H, m), 6.95 (1H, d, J=7.9 Hz), 6.99 (1H, d, J=2.8 Hz), 7.15 (1H, d, J=8.3 Hz), 7.24 (1H, t, J=7.9 Hz).

Example 23

(R)-2-t-butoxycarbonylamino-5-[2-chloro-4-(3-chlorophenylthio)phenyl]-2-methylpentan-1-ol

[Chemical formula 57]

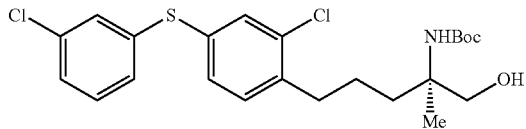

The compound of Example 8 was reacted in the same manner as in Example 11 to obtain an ester, which was then reacted in the same manner as in Example 15 to obtain the target product as a colorless oil.

$^1$H-NMR (CDCl$_3$, 400 MHz): δ 1.14 (3H, s), 1.43 (9H, s), 1.58-1.74 (3H, m), 1.79-1.92 (1H, m), 2.73 (2H, t, J=6.7 Hz), 3.61 (1H, d, J=12 Hz), 3.64 (1H, d, J=12 Hz), 4.08 (1H, br s), 4.57 (1H, br s), 7.17-7.27 (6H, m), 7.37 (1H, s).

ESIMS (+): 470 [M+H]$^+$.

Example 24

(R)-2-t-butoxycarbonylamino-5-[2-fluoro-4-(3-trifluoromethylphenylthio)phenyl]-2-methylpentan-1-ol

[Chemical formula 58]

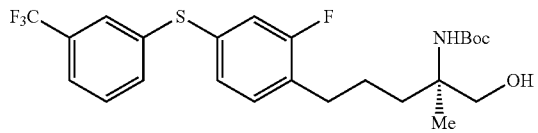

The compound of Example 12 was reacted in the same manner as in Example 15 to obtain the target product as a colorless oil.

$^1$H-NMR (CDCl$_3$, 400 MHz): δ 1.14 (3H, s), 1.42 (9H, s), 1.55-1.74 (3H, m), 1.75-1.85 (1H, m), 2.65 (2H, t, J=6.7 Hz), 3.58-3.64 (2H, m), 4.03 (1H, br s), 4.55 (1H., br s), 7.04 (1H, dd, J=9.8 Hz, 1.8 Hz), 7.10 (1H, dd, J=7.9 Hz, 1.8 Hz), 7.17 (1H, t, J=7.9 Hz), 7.38-7.50 (3H, m), 7.54 (1H, br s).

Example 25

(R)-2-t-butoxycarbonylamino-5-[2-chloro-4-(3-trifluoromethylphenylthio)phenyl]-2-propylpentan-1-ol

[Chemical formula 59]

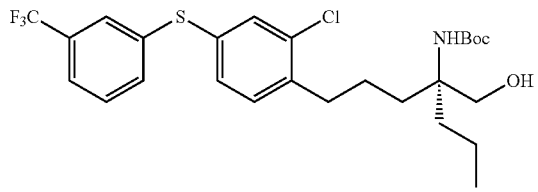

The compound of Example 14 was reacted in the same manner as in Example 15 to obtain the target product as a colorless oil.

$^1$H-NMR (CDCl$_3$, 400 MHz): δ 0.92 (3H, t, J=7.3 Hz), 1.42 (9H, s), 1.14-1.80 (8H, m), 2.72 (2H, t, J=7.3 Hz), 3.62 (1H, d, J=12 Hz), 3.66 (1H, d, J=12 Hz), 4.54 (1H, br s), 7.16-7.22 (2H, m), 7.39 (1H, s), 7.40-7.48 (3H, m), 7.55 (1H, br s).

FABMS (+): 532 [M+H]$^+$.

Example 26

(R)-2-amino-5-[2-chloro-4-(3-trifluoromethylphenoxy)phenyl]-2-methylpentan-1-ol hydrochloride

[Chemical formula 60]

To the compound of Example 15 (6.50 g) was added a 10 w/w % hydrogen chloride solution in methanol (methanol containing hydrogen chloride, 67 mL), and the resultant mixture was stirred for 1 hour at room temperature, and then left overnight at room temperature. The solvent was then evaporated to obtain the target product (5.15 g) as a colorless amorphous.

$^1$H-NMR (DMSO-d$_6$, 400 MHz): δ 1.07 (3H, s), 1.46-1.64 (4H, m), 2.62-2.72 (2H, m), 3.31-3.36 (2H, m), 7.03 (1H, dd, J=7.9, 2.4 Hz), 7.20 (1H, d, J=2.4 Hz), 7.30 (1H, d, J=7.9 Hz), 7.34 (1H, s), 7.39 (1H, d, J=7.9 Hz), 7.52 (1H, d, J=7.9 Hz), 7.63 (1H, t, J=7.9 Hz).

HREIMS (+): 388.1281 (Calcd. for C$_{19}$H$_{21}$NClF$_3$O$_2$: 388.1291).

Optical Rotation: $[\alpha]_D^{23}$ −2.74 (c 0.63, CHCl$_3$).

Example 27

(R)-2-amino-5-[2-chloro-4-(3-trifluoromethylphenylthio)phenyl]-2-methylpentan-1-ol hydrochloride

[Chemical formula 61]

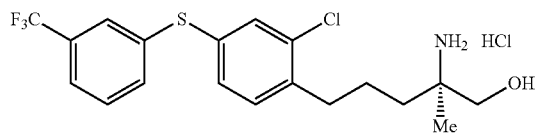

The compound of Example 16 was reacted in the same manner as in Example 26 to obtain the target product as a white powder.

$^1$H-NMR (DMSO-d$_6$, 400 MHz): δ 1.09 (3H, s), 1.49-1.63 (4H, m), 2.65-2.71 (2H, br s), 3.34 (1H, d, J=12 Hz), 3.38 (1H, d, J=12 Hz), 7.34 (1H, dd, J=7.9 Hz, 2.4 Hz), 7.41 (1H, d, J=7.9 Hz), 7.49 (1H, d, J=2.4 Hz), 7.55 (1H, d, J=7.9 Hz), 7.61 (1H, d, J=2.4 Hz), 7.67 (1H, d, J=7.9 Hz), 7.53-7.74 (3H, br s).

ESIMS (+): 404 [M+H]$^+$.

Elemental Analysis: Measured: C 51.65%, H 4.86%, N 2.86%, Calcd. for C$_{19}$H$_2$ClF$_3$NOS.HCl: C 51.82%, H 5.04%, N 3.18%.

Optical Rotation: $[\alpha]_D^{23}$ −3.45 (c 1.00, CHCl$_3$).

Example 28

(R)-2-amino-4-[2-chloro-4-(3-trifluoromethylphenoxy)phenyl]-2-methylbutan-1-ol hydrochloride

[Chemical formula 62]

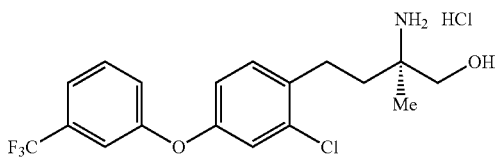

The compound of Example 17 was reacted in the same manner as in Example 26 to obtain the target product as a white powder.

$^1$H-NMR (DMSO-$d_6$, 400 MHz): δ 1.24 (3H, s), 1.70-1.80 (2H, m), 2.71 (2H, t, J=8.6 Hz), 3.44 (1H, dd, J=11 Hz, 4.9 Hz), 3.50 (1H, dd, J=11 Hz, 4.9 Hz), 5.54 (1H, t, J=4.9 Hz), 7.04 (1H, dd, J=8.6, 2.4 Hz), 7.21 (1H, d, J=2.4 Hz), 7.31 (1H, dd, J=8.6, 2.4 Hz), 7.35 (1H, br s), 7.41 (1H, d, J=8.6 Hz), 7.52 (1H, d, J=7.9 Hz), 7.63 (1H, t, J=7.9 Hz), 7.95 (3H, br s).

FABMS (+): 374 [M+H]$^+$.

Elemental Analysis: Measured: C 52.38%, H 4.80%, N 3.42%, Calcd. for $C_{18}H_{19}ClF_3NO_2 \cdot HCl$: C 52.70%, H 4.91%, N 3.41%.

Example 29

(R)-2-amino-4-[2-chloro-4-(3-trifluoromethylphenylthio)phenyl]-2-methylbutan-1-ol hydrochloride

[Chemical formula 63]

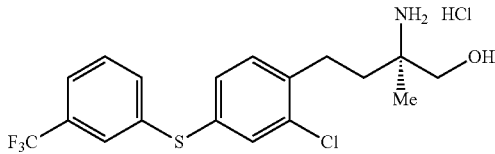

The compound of Example 18 was reacted in the same manner as in Example 26 to obtain the target product as a white powder.

$^1$H-NMR (DMSO-$d_6$, 400 MHz): δ 1.22 (3H, s), 1.66-1.83 (2H, m), 2.72 (2H, t, J=8.6 Hz), 3.42 (1H, dd, J=11.0, 7.9 Hz), 3.49 (1H, dd, J=11.0, 7.9 Hz), 5.54 (1H, t, J=4.9 Hz), 7.36 (1H, dd, J=7.9, 1.8 Hz), 7.42 (1H, d, J=7.9 Hz), 7.50 (1H, d, J=1.8 Hz), 7.53-7.64 (3H, m), 7.67 (1H, d, J=7.9 Hz), 7.82 (3H, br s).

FABMS (+): 390 [M+H]$^+$.

Elemental Analysis: Measured: C 50.47%, H 4.65%, N 3.36%, Calcd. for $C_{18}H_{19}ClF_3NOS \cdot HCl$: C 50.71%, H 4.73%, N 3.29%.

Optical Rotation: $[\alpha]_D^{27}$ +5.78 (c 0.33, CHCl$_3$).

Example 30

(R)-2-amino-4-[2-chloro-4-(3-ethylphenylthio)phenyl]-2-methylbutan-1-ol hydrochloride

[Chemical formula 64]

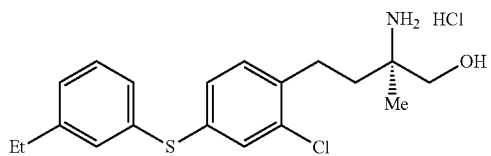

The compound of Example 19 was reacted in the same manner as in Example 26 to obtain the target product as a white powder.

$^1$H-NMR (DMSO-$d_6$, 400 MHz): δ 1.14 (3H, t, J=7.3 Hz), 1.22 (3H, s), 1.67-1.81 (2H, m), 2.59 (2H, q, J=7.3 Hz), 2.69 (2H, t, J=8.6 Hz), 3.42 (1H, dd, J=11.6, 5.5 Hz), 3.48 (1H, dd, J=11.6, 5.5 Hz), 5.52 (1H, t, J=4.9 Hz), 7.16-7.22 (2H, m), 7.26-7.27 (2H, m), 7.30-7.35 (2H, m), 7.93 (3H, br s).

0 ESIMS (+): 350 [M+H]$^+$.

Elemental Analysis: Measured: C 58.90%, H 6.42%, N 3.59%, Calcd. for $C_{19}H_{24}ClNOS \cdot HCl$: C 59.06%, H 6.52%, N 3.63%.

Example 31

(R)-2-amino-5-[2-chloro-4-(3-methylphenoxy)phenyl]-2-methylpentan-1-ol hydrochloride

[Chemical formula 65]

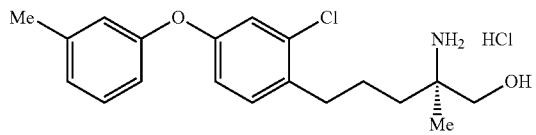

The compound of Example 20 was reacted in the same manner as in Example 26 to obtain the target product as a colorless amorphous.

$^1$H-NMR (DMSO-$d_6$, 400 MHz): δ 1.11 (3H, s), 1.57 (4H, brs), 2.29 (3H, s), 2.64 (2H, brs), 3.35-3.39 (2H, m), 5.45 (1H, t, J=4.9 Hz), 6.81 (1H, dd, J=8.6, 2.4 Hz), 6.85 (1H, s), 6.92 (1H, dd, J=8.6, 2.4 Hz), 6.99 (1H, d, J=8.6 Hz), 7.03 (1H, d, J=2.4 Hz), 7.28 (1H, t, J=8.6 Hz), 7.34 (1H, d, J=8.6 Hz), 7.77 (3H, brs).

HRESIMS (+): 334.15655 (Calcd. for $C_{19}H_{25}ClNO_2$: 334.15738).

Optical Rotation: $[\alpha]_D^{26.7}$ −5.75 (c 0.60, CHCl$_3$).

Example 32

(R)-2-amino-5-[2-chloro-4-(3-ethylphenylthio)phenyl]-2-methylpentan-1-ol hydrochloride

[Chemical formula 66]

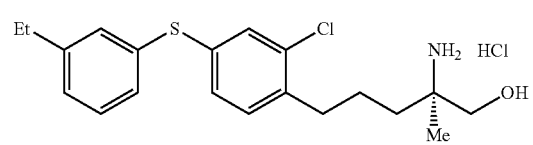

The compound of Example 21 was reacted in the same manner as in Example 26 to obtain the target product as a colorless oil.

$^{1}$H-NMR (DMSO-$d_6$, 400 MHz): δ 1.10 (3H, s), 1.15 (3H, t, J=7.3 Hz), 1.52-1.58 (4H, m), 2.59 (2H, q, J=7.3 Hz), 2.62-2.66 (2H, m), 3.32-3.39 (2H, m), 5.43 (1H, br), 7.15-7.22 (3H, m), 7.26 (2H, d, J=1.8 Hz), 7.32 (2H, dd, J=7.3, 1.8 Hz), 7.81 (3H, br s).

HRESIMS (+): 364.15051 (Calcd. for $C_{20}H_{27}ClNOS$: 364.15019).

Example 33

(R)-2-amino-5-[2-chloro-4-(3-propylphenoxy)phenyl]-2-methylpentan-1-ol hydrochloride

[Chemical formula 67]

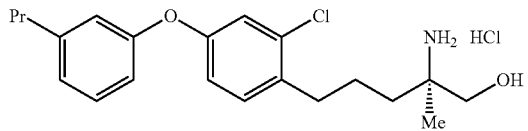

The compound of Example 22 was reacted in the same manner as in Example 26 to obtain the target product as a colorless amorphous.

$^{1}$H-NMR (DMSO-$d_6$, 400 MHz): δ 0.86 (3H, t, J=7.3 Hz), 1.11 (3H, s), 1.51-1.61 (6H, m), 2.53 (2H, t, J=7.3 Hz), 2.63 (2H, t, J=6.7 Hz), 3.34-3.42 (2H, m), 5.45 (1H, t, J=4.9 Hz), 6.81 (1H, ddd, J=7.9, 1.8, 0.9 Hz), 6.87 (1H, t, J=1.8 Hz), 6.91 (1H, dd, J=8.6, 2.4 Hz), 7.00 (1H, d, J=7.9 Hz), 7.02 (1H, d, J=2.4 Hz), 7.30 (1H, t, J=7.9 Hz), 7.34 (1H, d, J=8.6 Hz), 7.85 (3H, br s).

ESIMS(+): 362 [M+H]$^+$.

HRESIMS(+): 362.19198 (Calcd. for $C_{21}H_{29}ClNO_2$: 362.18868).

Optical Rotation: $[α]_D^{25.1}$ −4.46 (c 1.27, CHCl$_3$).

Example 34

(R)-2-amino-5-[2-chloro-4-(3-chlorophenylthio)phenyl]-2-methylpentan-1-ol hydrochloride

[Chemical formula 68]

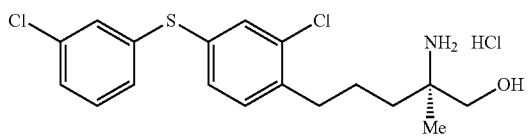

The compound of Example 23 was reacted in the same manner as in Example 26 to obtain the target product as a colorless amorphous $^{1}$H-NMR (DMSO-$d_6$, 400 MHz): δ 1.10 (3H, s), 1.49-1.64 (4H, m), 2.68 (2H, br s), 3.33 (1H, dd, J=12, 4.9 Hz), 3.38 (1H, dd, J=12, 4.9 Hz), 5.45 (1H, t, J=4.9 Hz), 7.26 (1H, dt, J=7.3, 1.8 Hz), 7.30-7.43 (5H, m), 7.45 (1H, d, J=1.8 Hz), 7.77 (3H, br s).

HREIMS (+): 370.0 799 (Calcd. for $C_{18}H_{21}Cl_2NOS$: 370.0799).

Optical Rotation: $[α]_D^{27}$ −3.81 (c 0.50, CHCl$_3$).

Example 35

(R)-2-amino-5-[2-fluoro-4-(3-trifluoromethylphenylthio)phenyl]-2-methylpentan-1-ol hydrochloride

[Chemical formula 69]

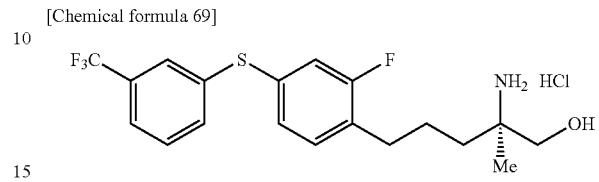

The compound of Example 24 was reacted in the same manner as in Example 26 to obtain the target product as a colorless amorphous.

$^{1}$H-NMR (DMSO-$d_6$, 400 MHz): δ 1.09 (3H, s), 1.48-1.61 (4H, m), 2.57-2.64 (2H, br s), 3.32 (1H, dd, J=11, 4.9 Hz), 3.37 (1H, dd, J=11, 4.9 Hz), 5.44 (1H, t, J=4.9 Hz), 7.20 (1H, dd, J=7.9, 1.8 Hz), 7.26 (1H, dd, J=9.8, 1.8 Hz), 7.37 (1H, t, J=7.9 Hz), 7.54-7.68 (4H, m), 7.74 (3H, br s).

HRESIMS (+): 388.1345 (Calcd. for $C_{19}H_{22}F_4NOS$: 388.1358).

Optical Rotation: $[α]_D^{24}$ −3.23 (c 0.69, CHCl$_3$)

Example 36

(R)-2-amino-5-[2-chloro-4-(3-trifluoromethylphenylthio)phenyl]-2-propylpentan-1-ol hydrochloride

[Chemical formula 70]

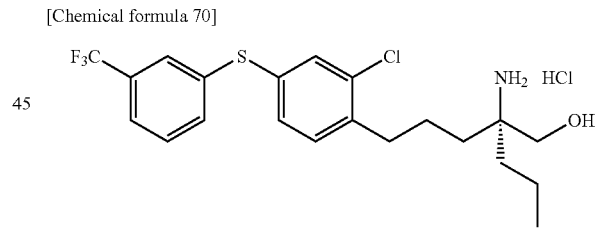

The compound of Example 25 was reacted in the same manner as in Example 26 to obtain the target product as a white powder.

$^{1}$H-NMR (DMSO-$d_6$, 400 MHz): δ 0.84 (3H, t, J=7.3 Hz), 1.20 (2H, q, J=7.3 Hz), 1.36-1.63 (6H, m), 2.68 (2H, t, J=7.3 Hz), 3.36 (2H, d, J=4.9 Hz), 5.40 (1H, d, J=4.9 Hz), 7.35 (1H, dd, J=7.9 Hz, 1.8 Hz), 7.42 (1H, d, J=7.9 Hz), 7.50 (1H, d, J=1.8 Hz), 7.55 (1H, d, J=7.9 Hz), 7.58-7.63 (2H, m), 7.67 (1H, d, J=7.9 Hz), 7.69 (3H, br s).

FABMS (+): 432 [M+H]$^+$.

Elemental Analysis: Measured: C 53.46%, H 5.62%, N 2.98%, Calcd. for $C_{21}H_{25}ClF_3NOS·HCl$: C 53.85%, H 5.59%, N 2.99%.

Optical Rotation: $[α]_D^{23}$ +3.85 (c 0.63, CHCl$_3$).

Example 37

(R)-2-amino-5-[2-chloro-4-(3-trifluoromethylphenylthio)phenyl]-2-methylpentan-1-ol

[Chemical formula 71]

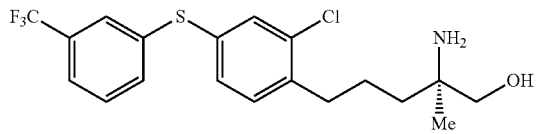

To a solution of the compound of Example 27 (9.3 g) in ethyl acetate (450 mL) was added saturated aqueous sodium hydrogen carbonate solution (450 mL), and the resultant solution was stirred at room temperature for 10 minutes. The organic layer was washed with water and saturated brine in that order, and then dried over anhydrous sodium sulfate. The solvent was evaporated, and the resultant residue was purified by NH-silica gel column chromatography (ethyl acetate: methanol=4:1) to obtain the target product (8.9 g) as a white powder.

$^1$H-NMR (DMSO-$d_6$, 400 MHz): δ 0.85 (3H, s), 1.21 (2H, br s), 1.28 (2H, t, J=8.6 Hz), 1.46-1.67 (2H, m), 2.65 (2H, t, J=8.6 Hz), 3.06 (2H, br s), 4.49 (1H, br s), 7.32 (1H, dd, J=7.9, 1.8 Hz), 7.40 (1H, d, J=9.8 Hz), 7.47 (1H, d, J=1.8 Hz), 7.54 (1H, dd, J=6.7, 1.8 Hz), 7.56-7.62 (2H, m), 7.65 (1H, dd, J=6.7, 1.8 Hz).

ESIMS (+): 404 [M+H]$^+$.

Elemental Analysis: Measured: C 56.26%, H 5.14%, N 3.40%, Calcd. for $C_{19}H_{21}ClF_3NOS$: C 56.50%, H 5.24%, N 3.47%.

Example 38

Diethyl 2-{3-[2-chloro-4-(3-trifluoromethylphenylthio)phenyl]propyl}-2-methylmalonate

[Chemical formula 72]

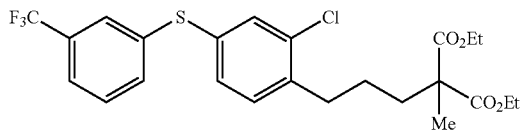

2-Chloro-1-(3-iodopropyl)-4-(3-trifluoromethylphenylthio) benzene and diethyl 2-methylmalonate were reacted according to the same procedures as in Example 152 of WO 04026817 to obtain the target product as a colorless oil.

$^1$H-NMR (CDCl$_3$, 400 MHz): δ 1.25 (6H, t, J=7.4 Hz), 1.40 (3H, s), 1.51-1.63 (2H, m), 1.90-1.97 (2H, m), 2.73 (2H, t, J=7.9 Hz), 4.17 (4H, q, J=7.4 Hz), 7.17-7.23 (2H, m), 7.38 (1H, d, J=2.2 Hz), 7.39-7.44 (2H, m), 7.45-7.50 (1H, m), 7.55 (1H, s).

EIMS (+): 502 [M]$^+$.

Example 39

(±)-5-[2-chloro-4-(3-trifluoromethylphenylthio)phenyl]-2-ethoxycarbonyl-2-methylpentanoic acid

[Chemical formula 73]

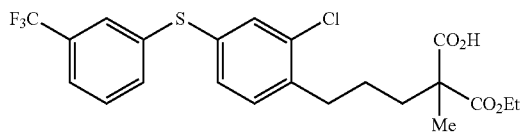

To a solution of the compound of Example 38 (16.8 g) in ethanol (167 mL) was added potassium hydroxide (2.40 g), and the resultant solution was stirred at 50° C. for 24 hours. To the reaction solution was added water, neutralized with 2 mol/L aqueous hydrochloric acid, and extracted with ethyl acetate. The organic layer was washed with water and saturatedbrine in that order, and then dried over anhydrous sodium sulfate. The solvent was evaporated, and the resultant residue was purified by silica gel column chromatography (hexane ethyl acetate=1:1) to obtain the target product (11.2 g) as a colorless oil.

$^1$H-NMR (CDCl$_3$, 400 MHz): δ 1.26 (3H, t, J=7.4 Hz), 1.47 (3H, s), 1.55-1.66 (2H, m), 1.87-2.06 (2H, m), 2.73 (2H, t, J=7.9 Hz), 4.22 (2H, q, J=7.4 Hz), 7.18 (1H, d, J=7.9 Hz), 7.20 (1H, dd, J=7.9, 1.8 Hz), 7.38 (1H, d, J=1.8 Hz), 7.39-7.44 (2H, m), 7.45-7.50 (1H, m), 7.54 (1H, s).

ESIMS (+) 475 [M+H]$^+$.

Example 40

Ethyl (±)-5-[2-chloro-4-(3-trifluoromethylphenylthio)phenyl]-2-methoxycarbonylamino-2-methylpentanoate

[Chemical formula 74]

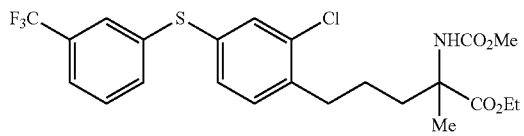

To a solution of the compound of Example 39 (15.8 g) in benzene (166 mL) was added diphenylphosphoryl azide (7.86 mL) and triethylamine (6.01 mL), and the resultant solution was heated to reflux for 1.5 hours. The temperature of the reaction solution was returned to room temperature, and methanol (20 mL) was added dropwise over 20 minutes. The resultant solution was heated to reflux for 30 minutes, and then further sodium methoxide (3.58 g) was added. The resultant solution was heated to reflux for 1.5 hours. To the reaction solution was added saturated aqueous ammonium chloride, and extracted with ethyl acetate. The organic layer was washed with water and saturatedbrine in that order, and then dried over anhydrous sodium sulfate. The solvent was evaporated, and the resultant residue was purified by silica gel column chromatography (hexane ethyl acetate=5:1) to obtain the target product (15.6 g) as a colorless oil.

$^1$H-NMR (CDCl$_3$, 400 MHz): δ 1.25 (3H, t, J=7.3 Hz), 1.32-1.47 (1H, m), 1.52-1.67 (1H, m), 1.57 (3H, s), 1.80-1.90

(1H, m), 2.20-2.37 (1H, m), 2.62-2.76 (2H, m), 3.64 (3H, s), 4.15-4.25 (2H, m), 5.62 (1H, br s), 7.16 (1H, d, J=7.9 Hz), 7.20 (1H, dd, J=7.9, 1.8 Hz), 7.38 (1H, d, J=1.8 Hz), 7.40-7.44 (2H, m), 7.45-7.50 (1H, m), 7.55 (1H, s).
ESIMS (+): 504 [M+H]$^+$.

Example 41

(±)-5-[2-chloro-4-(3-trifluoromethylphenylthio)phenyl]-2-methoxycarbonylamino-2-methylpentan-1-ol

[Chemical formula 75]

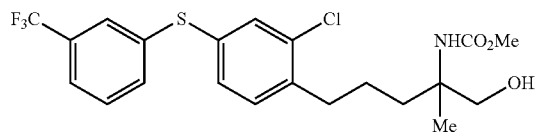

To a solution of the compound of Example 40 (15.6 g) in THF (249 mL) was added under ice cooling lithium borohydride (3.75 g), and then ethanol (16.6 mL) was added dropwise. The resultant solution was then stirred for 1 hour under ice cooling. To The reaction solution was added 10% aqueous citric acid, extracted with ethyl acetate, washed with water and saturated brine in that order, and then dried over anhydrous sodium sulfate. The solvent was evaporated, and the resultant residue was purified by silica gel column chromatography (hexane:ethyl acetate=1:1) to obtain the target product (12.9 g) as a colorless oil.
$^1$H-NMR (CDCl$_3$, 400 MHz): δ 1.18 (3H, s), 1.54-1.74 (3H, m), 1.78-1.89 (1H, m), 2.73 (2H, t, J=7.9 Hz), 3.63 (3H, s), 3.56-3.70 (2H, m), 4.23 (1H, br s), 7.17-7.22 (2H, m), 7.38-7.50 (4H, m), 7.54 (1H, s).
ESIMS (+): 462 [M+H]$^+$.

Example 42

(±)-2-t-butoxycarbonylamino-5-[2-chloro-4-(3-trifluoromethylphenylthio)phenyl]-2-methylpentan-1-ol

[Chemical formula 76]

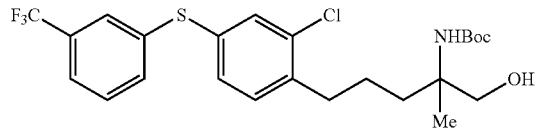

To a solution of the compound of Example 41 (12.9 g) in THF (60 mL) and methanol (120 mL) was added under ice cooling 5 mol/L aqueous potassium hydroxide solution (60 mL), and the resultant solution was heated to reflux for 86 hours. To the reaction solution was added water, extracted with ethyl acetate, washed with water and saturated brine in that order, and then dried over anhydrous sodium sulfate. The extract was concentrated, the residue was dissolved in 1,4-dioxane (279 mL), and the resultant solution was charged with di-tert-butoxydicarbonate (9.13 g). The solution was stirred at room temperature for 2 hours and then left to stand at room temperature overnight. The reaction solution was added water, extracted with ethyl acetate, washed with water and saturated brine in that order, and then dried over anhydrous sodium sulfate. The solvent was evaporated, and the resultant residue was purified by silica gel column chromatography (hexane:ethyl acetate=2:1) to obtain the target product (13.0 g) as a colorless oil.
$^1$H-NMR (CDCl$_3$, 400 MHz): δ 1.14 (3H, s), 1.42 (9H, s), 1.53-1.74 (3H, m), 1.79-1.92 (1H, m), 2.74 (2H, t, J=7.9 Hz), 3.58-3.69 (2H, m), 4.05 (1H, brs), 4.57 (1H, brs), 7.20-7.22 (2H, m), 7.38-7.50 (4H, m), 7.54 (1H, s).
ESIMS (+): 504 [M+H]$^+$.

Examples 43 and 44

(+)-2-t-butoxycarbonylamino-5-[2-chloro-4-(3-trifluoromethylphenylthio)phenyl]-2-methylpentan-1-ol and (−)-2-t-butoxycarbonylamino-5-[2-chloro-4-(3-trifluoromethylphenylthio)phenyl]-2-methylpentan-1-ol The compound of Example 42 was subjected to optical resolution using high performance liquid chromatography (CHIRALCEL OJ-H, hexane:isopropanol:diethylamine=98:2:0.1 (v/v), measurement wavelength: UV 278 nm, flow rate: 1.0 mL/min). From the pre-elution portion, an $[\alpha]_D^{25}$+15.08 (c 0.63, CHCl$_3$) colorless oil was obtained (Example 43), and from the post-elution portion, an $[\alpha]_D^{26}$−13.91 (c 0.63, CHCl$_3$) colorless oil was obtained (Example 44).

Example 45

(−)-2-Amino-5-[2-chloro-4-(3-trifluoromethylphenylthio)phenyl]-2-methylpentan-1-ol hydrochloride The compound of Example 43 was reacted in the same manner as in Example 26 to obtain the target product as a white powder.
ESIMS (+): 404 [M+H]$^+$;
Optical Rotation: $[\alpha]_D^{25}$−4.48 (c 1.00, CHCl$_3$).
Next, results which support the utility of the compound of the present invention will be shown by experiment examples.

Experiment Example 1

Activity On Total Number of White Blood Cells in Mouse Peripheral Blood

The test compounds were dissolved or suspended in DMSO, and then a physiological saline solution was added to make dosing solutions (DMSO final concentration 1%). If the dosing solutions were not in a dissolved or a uniform suspended state, Tween 80 was added so that the final concentration thereof was 0.01 to 0.1%. The resultant solutions were then sonicated to form a fine suspension. These test compound solutions were intraperitoneally administered in respective amounts of 0.1 mL or 0.2 mL per 10 g of body weight to BALB/cCrSlc male mice (8 to 14 weeks old, Japan SLC). For the control group, only a solvent having the same composition as that used in the preparation of the test compounds was administered in the same manner. Six hours after administration of the test compound solutions, blood was collected from the postcava under ether anesthesia (10 µL of 10% EDTA was added as an anticoagulant). Measurement of the total number of white blood cells was carried out using the automated blood cell counting apparatus Sysmex F-820 (Sysmex).

Here, compounds having an inhibition ratio of 60% or more were marked as "+++", compounds having an inhibition ratio of less than 60% but more than or equal to 50% were marked as "++", and compounds having an inhibition ratio of less than 50% but more than or equal to 40% were marked as "+". Furthermore, the inhibition ratios are the results from a dose of 0.3 mg/kg ("[ ]" are the results from 3 mg/kg). The results are shown in Table 1.

TABLE 1

| Example No. | Inhibition Ratio |
|---|---|
| 26 | [+] |
| 27 | + |
| 28 | ++ |
| 29 | +++ |
| 36 | [++] |

[3 mg/kg]

Experiment Example 2

Inhibition Activity of the Test Compounds On Mouse Host-Versus-Graft Rejection Reaction Experiment example 2 was carried out by referring to the methods described in Transplantation, Vol. 55, No. 3, pp. 578 to 591, 1993. The spleens from BALB/c male mice which were 6 to 23 weeks old (Japan SLC) were collected. The spleens were extracted in RPMI-1640 medium (Sigma), and then turned into a spleen cell suspension by grinding them with 2 glass slides and then passing the ground matter through a strainer (70 microns, Falcon). The spleen cell suspensions were centrifuged, and the supernatants were removed. Then, an ammonium chloride-tris isotonic buffer solution was added, and the red blood cells were hemolyzed. After centrifuging and washing 3 times with RPMI-1640 medium, the cells were suspended in RPMI-1640 medium. Mitomycin C (Kyowa Hakko) was added thereto so that the final concentration was 25 μg/mL, and the cells were incubated for 30 minutes at 37° C. under 5% $CO_2$. After centrifuging and washing 3 times with RPMI-1640 medium, the cells were suspended in RPMI-1640 medium so that the concentration was $2.5 \times 10^8$ cells/mL. These cells were used as a stimulator cell suspension. 20 μL ($5 \times 10^6$ cells/mouse) of the stimulator cell suspension was injected subcutaneously into the right hind-foodpad of C3H/HeN male mice which were 6 to 11 weeks old (Clea Japan) using a 27G needle and a microsyringe (Hamilton). For the normal control group, RPMI-1640 medium only was injected. After 4 days, the right popliteal lymph nodes were extracted, and their weight was measured using Mettler AT201 electronic scales (Mettler Toledo). From the day of the stimulator cell suspensions being injected to 3 days thereafter, the test compounds were intraperitoneally administered on consecutive days once per day, for a total of 4 times. For the control group, only a solvent having the same composition as that used in the preparation of the test compounds was administered in the same manner. The results are shown in Table 2. As the solvent, basically a physiological saline containing 0.5% DMSO was used (suitably adjusted according to the solubility of the compound).

The inhibition ratio was calculated using the following equation.

$$\text{Inhibition ratio} = \frac{\left(\begin{array}{c}\text{Right Popliteal Lymph}\\\text{Node's Weight}\\\text{of the Positive Control Group}\end{array}\right) - \left(\begin{array}{c}\text{Right Popliteal Lymph}\\\text{Node's Weight}\\\text{of the Test Compound Group}\end{array}\right)}{\left(\begin{array}{c}\text{Right Popliteal Lymph}\\\text{Node's Weight}\\\text{of the Positive Control Group}\end{array}\right) - \left(\begin{array}{c}\text{Right Popliteal Lymph}\\\text{Node's Weight}\\\text{of the Normal Control Group}\end{array}\right)} \times 100$$  [Equation 1]

Compounds having an $ED_{50}$ value of less than 0.1 mg/kg were marked as "+++", compounds having an $ED_{50}$ value of less than 1 mg/kg but more than or equal to 0.1 mg/kg were marked as "++", and compounds having an $ED_{50}$ value of less than 10 mg/kg but more than or equal to 1 mg/kg were marked as "+".

TABLE 2

| Example No. | $ED_{50}$ |
|---|---|
| 26 | ++ |
| 27 | +++ |
| 28 | + |
| 29 | ++ |
| 32 | ++ |
| 35 | ++ |
| 36 | ++ |

Experiment Example 3

Activity of the Test Compounds On Rat Skin Graft Model>

Using a rat skin graft model, activity on the rejection reaction was investigated. An allogenic skin graft for rats having a matched major histocompatibility complex (MHC) was carried out by referring to the methods described in a publication (Am. J. Med. Technol.; 36, 149-157, 1970, Transplant. Proc.; 28, 1056 to 1059, 1996) etc.

Skin from the abdomen of a LEW/CrlCrlj rat serving as the donor (male, 5 weeks old, Japan Charles River) was peeled away, and the panniculus carnosus muscle layer under the skin was removed. Then, a 1.8 cm×1.8 cm skin specimen (graft) was prepared. Next, a F344/DuCrlCrlj rat serving as the recipient (male, 5 weeks old, Japan Charles River) was anesthetized by intraperitoneal administration of 40 mg/kg of sodium pentobarbital (nembutal injection, Dainippon Sumitomo Pharma). The hair of the back of the rat was shorn off by electric clippers, and then the remaining hair was further shaved off using a razor. Then, a 1.8 cm×1.8 cm mark was made on the back of the rat, and a shallow cut was made along the mark with a scalpel. Next, the skin was peeled away along this cut by tweezers to produce a graft bed. Several drops of sterile physiological saline solution (Otsuka normal saline, Otsuka Pharmaceutical) were dropped onto the graft bed, and then wiped away with gauze. Several drops of penicillin (crystalline penicillin GpotassiumMeiji, Meiji Seika) were then dropped thereon. Next, the graft was placed on the graft bed. After absorbing excess moisture with sterile gauze, a first-aid bandaid was stuck over the graft. Furthermore, an adhesive bandage was wrapped around the trunk of the rat. On the third day after the operation, a new adhesive bandage was wrapped thereover. On the fifth day after the operation, the bandaid and the bandages were cut open with scissors and removed. Observation of the graft was carried out on consecutive days from when the bandaid was removed (from the fifth day). A determination of graft rejection was made when 90% or more of the graft had died and tuned brown. The number of days from grafting until rejection was confirmed was taken as the survival period. The mean value of the survival period for each group was calculated as the mean survival time (MST). Investigation was carried out with 5 animals per group. All of the rats were housed in individual cages. The test compounds were dissolved in ultra-pure water, and were orally administered once a day, on consecutive days, from the graft day. For the control group, ultra-pure water was administered in the same manner.

The results are shown in Table 3. The control group MST was 8.8 days. Those grafts of animals to which the immunosuppressive agent cyclosporin (CsA) had been administered at 30 mg/kg were considered to have survived (MST: 28 days or more) throughout the observation period. In Example 27, a survival period extension effect of the graft was found by individual administration.

Next, the effects of Example 27(0.3 to 10 mg/kg) in combination with CsA (10 mg/kg), in which survival throughout the observation period was not obtained by individual administration, were investigated. As a result of using these substances together, the MST was 26 days or more, thus confirming a clear combined effect.

TABLE 3

Survival Period Extension Effect of Allogenic Skin Graft for Rats

| Compound (mg/kg, oral administration) | Individual survival period (days) | MST (days) |
| --- | --- | --- |
| Control | 8, 8, 8, 9, 11 | 8.8 |
| CsA (10) | 11, 11, 12, 13, 14 | 12.2 |
| CsA (30) | 28<, 28<, 28<, 28<, 28< | 28< |
| Example 27 (3) | 11, 11, 12, 12, 13 | 11.8 |
| Example 27 (10) | 12, 12, 14, 14, 18 | 14 |
| Example 27 (30) | 12, 13, 21, 28<, 28< | 20.4< |
| Example 27 (0.3) + CsA (10) | 28<, 28<, 28<, 28<, 28< | 28< |
| Example 27 (1) + CsA (10) | 28<, 28<, 28<, 28<, 28< | 28< |
| Example 27 (3) + CsA (10) | 23, 23, 28<, 28<, 28< | 26< |
| Example 27 (10) + CsA (10) | 28<, 28<, 28<, 28<, 28< | 28< |

Experiment Example 4

Effect on Rat Lung Weight

Crlj:Wistar rats (male) 5 to 8 weeks old were used in the experiment. An aqueous solution of the test compounds was respectively orally administered in an amount of 0.5 mL per 100 g of rat body weight. The lungs were extracted 6 hours later, and the lung weight was measured.

Investigation of administering the compound of Example 26 up to a dose of 30 mg/kg and the compound of Example 27 up to a dose of 100 mg/kg showed that there were no effects whatsoever on lung weight.

As a result, it was confirmed that the compounds of Examples 26 and 27 are highly safe compounds with mitigated side effects.

INDUSTRIAL APPLICABILITY

According to the present invention, an amino alcohol derivative having excellent immunosuppressive activity and safety can be provided. The compound of the present invention is useful as a preventive or treatment agent for rejection in organ transplants or bone marrow transplants, a preventive or treatment agent for autoimmune diseases such as inflammatory bowel disease, systemic lupus erythematosus, Crohn's disease, nephrotic syndrome, glomerular sclerosis, glomerular nephritis, multiple sclerosis, and myasthenia gravis, a preventive or treatment agent for rheumatoid arthritis, a preventive or treatment agent for psoriasis, allergic contact dermatitis, and atopic dermatitis, a preventive or treatment agent for hepatitis, hepatic steatosis, toxic liver injury, liver cirrhosis-derived or diabetes mellitus-derived liver disease, a preventive or treatment agent for allergic rhinitis, allergic conjunctivitis and the like, and a preventive or treatment agent for pulmonary fibrosis, idiopathic interstitial pneumonia, and bronchial asthma.

The invention claimed is:

1. An amino alcohol derivative represented by the general formula (1a),

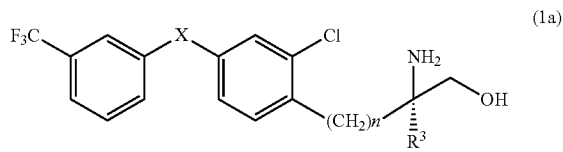

wherein $R^3$ represents a methyl group, X represents an oxygen atom or a sulfur atom, and n denotes 2 or 3, or a pharmaceutically acceptable salt thereof.

2. A pharmaceutical comprising the amino alcohol derivative, or a pharmaceutically acceptable salt thereof, according to claim 1 as an active ingredient.

3. The pharmaceutical according to claim 2, being an immunosuppressive agent.

4. The pharmaceutical according to claim 2, being a rejection treatment agent in organ transplants or bone marrow transplants.

5. A pharmaceutical comprising the amino alcohol derivative, or a pharmaceutically acceptable salt thereof, according to claim 1 and a calcineurin inhibitor in combination.

6. The amino alcohol derivative according to claim 1, wherein the compound represented by the general formula (1a) is,
(R)-2-amino-5-[2-chloro-4-(3-trifluoromethylphenylthio)phenyl]-2-methylpentan-1-ol, or a pharmaceutically acceptable salt thereof.

7. A pharmaceutical comprising the amino alcohol derivative, or a pharmaceutically acceptable salt thereof, according to claim 6 as an active ingredient.

8. A pharmaceutical comprising the amino alcohol derivative, or a pharmaceutically acceptable salt thereof, according to claim 6 and a calcineurin inhibitor in combination.

9. The amino alcohol derivative according to claim 1, wherein the compound represented by the general formula (1a) is a compound represented by the formula (1b),

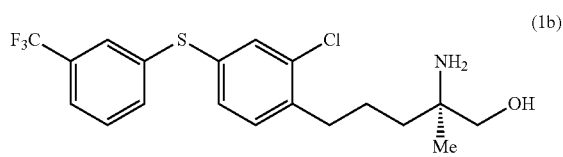

or a pharmaceutically acceptable salt thereof.

10. A pharmaceutical comprising the amino alcohol derivative, or a pharmaceutically acceptable salt thereof, according to claim 9 as an active ingredient.

11. An amino alcohol derivative represented by the general formula (1),

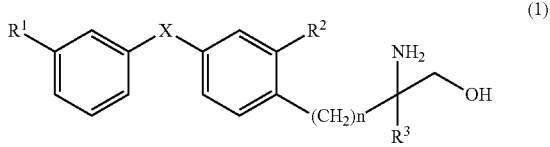

(1)

wherein $R^1$ represents a trifluoromethyl group, $R^2$ represents a chlorine atom, $R^3$ represents a methyl group, X represents an oxygen atom or a sulfur atom, and n denotes 2 or 3, or a pharmaceutically acceptable salt thereof, being obtainable by a step of allowing a compound represented by the general formula (2),

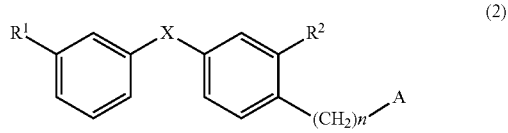

(2)

wherein $R^1$ represents a trifluoromethyl group, $R^2$ represents a chlorine atom, A represents a halogen atom, X represents an oxygen atom or a sulfur atom, and n denotes 2 or 3, and a compound represented by the general formula (10),

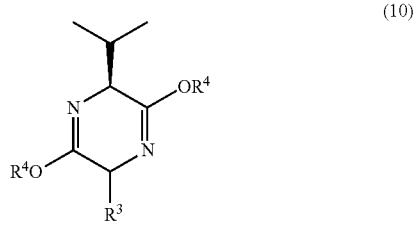

(10)

wherein $R^3$ represents a methyl group and $R^4$ represents an alkyl group having 1 to 6 carbon atoms to react in the presence of a base, and a step of subjecting the resultant product to acidolysis, then further protecting a nitrogen atom with a t-butoxycarbonyl group, reducing, and deprotecting the nitrogen atom.

12. A pharmaceutical comprising the amino alcohol derivative, or a pharmaceutically acceptable salt thereof, according to claim 11 as an active ingredient.

13. A pharmaceutical comprising the amino alcohol derivative, or a pharmaceutically acceptable salt thereof, according to claim 11 and a calcineurin inhibitor in combination.

14. (−)-2-Amino-5-[2-chloro-4-(3-trifluoromethylphenylthio)phenyl]-2-methylpentan-1-ol, or a pharmaceutically acceptable salt thereof.

15. A method for treating a rejection in organ transplantation or bone marrow transplantation in a patient, comprising administering to a patient in need thereof a therapeutically effective amount of an amino alcohol derivative represented by the general formula (1a),

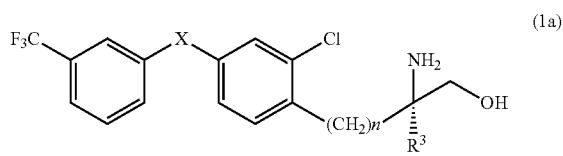

(1a)

wherein $R^3$ represents a methyl group, X represents an oxygen atom or a sulfur atom, and n denotes 2 or 3, or a pharmaceutically acceptable salt thereof, as an active ingredient.

16. The method according to claim 15, wherein the compound is (R)-2-amino-5- [2-chloro-4-(3-trifluoromethylphenylthio)phenyl]-2- methylpentan-1-ol, or a pharmaceutically acceptable salt thereof.

* * * * *